(12) United States Patent
Leininger et al.

(10) Patent No.: US 9,439,596 B2
(45) Date of Patent: Sep. 13, 2016

(54) METHOD AND APPARATUS FOR DETECTING SEIZURES

(71) Applicant: Brain Sentinel, Inc., San Antonio, TX (US)

(72) Inventors: James R. Leininger, San Antonio, TX (US); Russell M. Herring, San Antonio, TX (US); Michael R. Girouard, San Antonio, TX (US); Jose E. Cavazos, San Antonio, TX (US); Edward R. Jones, College Station, TX (US); William E. Broad, Littleton, CO (US)

(73) Assignee: Brain Sentinel, Inc., San Antonio, TX (US)

( * ) Notice: Subject to any disclaimer, the term of this patent is extended or adjusted under 35 U.S.C. 154(b) by 0 days.

(21) Appl. No.: 14/876,455

(22) Filed: Oct. 6, 2015

(65) Prior Publication Data

US 2016/0045150 A1    Feb. 18, 2016

Related U.S. Application Data

(63) Continuation of application No. 13/542,596, filed on Jul. 5, 2012, now Pat. No. 9,186,105.

(51) Int. Cl.
*A61B 5/00* (2006.01)
*A61B 5/0488* (2006.01)
*A61B 5/0492* (2006.01)
*A61B 5/0402* (2006.01)
*G06F 19/00* (2011.01)

(52) U.S. Cl.
CPC .......... *A61B 5/4094* (2013.01); *A61B 5/0004* (2013.01); *A61B 5/0488* (2013.01); *A61B 5/0492* (2013.01); *A61B 5/7267* (2013.01); *A61B 5/7271* (2013.01); *A61B 5/746* (2013.01); *A61B 5/0402* (2013.01); *A61B 5/7246* (2013.01); *G06F 19/3418* (2013.01)

(58) Field of Classification Search
CPC    A61B 5/0004; A61B 5/0488; A61B 5/4094; A61B 5/0402; A61B 5/7246; A61B 5/7267
See application file for complete search history.

(56) References Cited

U.S. PATENT DOCUMENTS 7,558,622 B2 *    7/2009    Tran .................... A61B 5/4076
                                                                  600/509

\* cited by examiner

*Primary Examiner* — Max Hindenburg
(74) *Attorney, Agent, or Firm* — The Pizarro Firm

(57) ABSTRACT

A method and apparatus for detecting seizures with motor manifestations including detecting EMG signals, isolating from the EMG signals spectral data for a plurality of frequency bands, and calculating a T-squared value there from. The T-squared values may be detected in real time, such as in a patient's home environment, and the T-squared data may be compared to a threshold T-squared value to determine whether an alarm is sent.

19 Claims, 22 Drawing Sheets

| Configure | View |
|---|---|
| Algorithm | ✓ Hotelling T-Square |
| Absolute Values | Principal Components |
| Filter Frequencies | |
| Filter Lag | |
| Client Episode | |

FIG. 9A

| Configure | View | |
|---|---|---|
| Algorithm | | |
| Absolute Values | | |
| Filter Frequencies | Band 1 | |
| Filter Lag | ✓ Band 2 | |
| Client Episode | Band 3 (narrow) | |

FIG. 9B

| Configure | View | |
|---|---|---|
| Algorithm | | |
| Absolute Values | | |
| Filter Frequencies | | |
| Filter Lag | ✓ 0.25 sec. | |
| Client Episode | 0.5 sec. | |
| | 1 sec. | |

FIG. 9C

| Configure | View | | |
|---|---|---|---|
| Algorithm | | A | |
| Absolute Values | | R | 075950 |
| Filter Frequencies | | G | 063906 |
| Filter Lag | | M | 090135 |
| Client Episode | | H | 095310 |
| | | Z | |

METHOD AND APPARATUS FOR DETECTING SEIZURES

PRIORITY DATA

This application is a continuation of U.S. application Ser. No. 13/542,596, which claims the benefit of U.S. Provisional Application No. 61/504,582, filed Jul. 5, 2011, the benefit of PCT Application No. PCT/US11/56601 filed Oct. 17, 2011, and the benefit of U.S. application Ser. No. 13/275,309 filed Oct. 17, 2011. The disclosure of U.S. Provisional Application No. 61/504,582, PCT Application No. PCT/US11/56601, and U.S. application Ser. No. 13/275,309 are herein wholly incorporated by reference.

BACKGROUND

A seizure may be characterized as abnormal or excessive synchronous activity in the brain. At the beginning of a seizure, neurons in the brain may begin to fire at a particular location. As the seizure progresses, this firing of neurons may spread across the brain, and in some cases, many areas of the brain may become engulfed in this activity. Seizure activity in the brain may cause the brain to send electrical signals through the peripheral nervous system to different muscles. For example, an electrical signal may originate in the central nervous system and initiate the propagation of an electrical signal through motor neurons. A motor neuron may, for example, communicate with a muscle through interaction with the motor end plate of a muscle fiber; thereby initiating an action potential and depolarization of muscle cells within a given motor unit. Depolarization typically results from the coordinated flow of ions, e.g., sodium and potassium cations, through channels within a muscle cell membrane. That is, changes in states of ion channels initiate a change in the permeability of a cell membrane, and subsequent redistribution of charged ions. Current flow through muscle cells may initiate a corresponding flow in the tissue above the muscle and thus an electrical signature at the surface of the skin.

Techniques designed for studying and monitoring seizures have typically relied upon electroencephalography (EEG), which characterizes electrical signals using electrodes attached to the scalp or head region of a seizure prone individual, or seizure patient. EEG electrodes may be positioned so as to measure such activity, that is, electrical activity originating from neuronal tissue. Compared to EEG, electromyography (EMG) is a little-used technique in which an electrode may be placed on or near the skin, over a muscle, to detect an electrical current or change in electric potential in response to redistribution of ions within muscle fibers.

Detecting an epileptic seizure using electroencephalography (EEG) typically requires attaching many electrodes and associated wires to the head and using amplifiers to monitor brainwave activity. The multiple EEG electrodes may be very cumbersome and generally require some technical expertise to apply and monitor. Furthermore, confirming a seizure requires observation in an environment provided with video cameras and video recording equipment. Unless used in a staffed clinical environment, such equipment is frequently not intended to determine if a seizure is in progress but rather provides a historical record of the seizure after the incident. Such equipment is usually meant for hospital-like environments where a video camera recording or caregiver's observation may provide corroboration of the seizure, and is typically used as part of a more intensive care regimen such as a hospital stay for patients who experience multiple seizures. A hospital stay may be required for diagnostic purposes or to stabilize a patient until suitable medication can be administered. Upon discharge from the hospital, a patient may be sent home with little further monitoring. However, at any time after being sent home the person may experience another seizure, perhaps fatal.

A patient should in some cases be monitored at home for some length of time in case another seizure should occur. Seizures with motor manifestations may have patterns of muscle activity that include rhythmic contractions of some, most, or all of the muscles of the body. A seizure could, for example, result in Sudden Unexplained Death in Epilepsy (SUDEP). The underlying causes of SUDEP are not well understood; however, some possible mechanisms causing SUDEP may include tonic activation of the diaphragm muscle so as to prevent breathing, neurogenic pulmonary edema, asystole, and other cardiac dysrhythmia. If a sleeping person experiences a seizure involving those conditions, then caregivers may not be aware that the seizure is occurring, and thus be unable to render timely aid.

While there presently exist ambulatory devices for diagnosis of seizures, they are EEG-based and are generally not designed or suitable for long-term home use or daily wearability. Other seizure alerting systems may operate by detecting motion of the body, usually the extremities. Such systems may generally operate on the assumption that while suffering a seizure, a person will move erratically and violently. For example, accelerometers may be used to detect violent extremity movements. However, depending upon the type of seizure, this assumption may or may not be true. Electrical signals sent from the brain during the seizure are frequently transmitted to many muscles simultaneously, which may result in muscles fighting each other and effectively canceling out violent movement. In other words, the muscles may work to make the person rigid rather than cause actual violent movement. Thus, the seizure may not be consistently detected with accelerometer-based detectors.

Accordingly, there is a need for an epileptic seizure method and apparatus that can be used in a non-institutional or institutional environment without many of the cumbersome electrodes to the head or extremities. Such an apparatus may be minimally intrusive, minimally interfere with daily activities and be comfortably used while sleeping. There is also a need for an epileptic seizure method and apparatus that accurately detects a seizure with motor manifestations and may alert one or more local and/or remote sites of the presence of a seizure. Furthermore, there is a need for an epileptic detection seizure method and apparatus that may be used in a home setting and which may provide robust seizure detection, even in the absence of violent motion, and which may be personalizable, e.g., capable of being tailored for an individual or specific population demographic.

SUMMARY

A method of detecting seizures with motor manifestations including the steps of detecting EMG signals for a time period, the time period comprising a reference period and a monitoring period; using digital filtering to isolate from the EMG signals spectral data for a plurality of frequencies bands selected from the range of about 2 Hz to about 1000 Hz; calculating a first T-squared value, the first T-squared value being determined from spectral data for the plurality of frequency ranges, from at least one part of the reference period; calculating a second T-squared value, the second T-squared value being determined from spectral data for the plurality of frequency ranges, from at least one part of the monitoring period; comparing the second T-squared value to the first T-squared value; and determining whether to trigger an alarm condition using said comparison of the first T-squared value to the second T-squared value.

A method of detecting seizures with motor manifestations including the steps of detecting EMG signals for a time period, the time period comprising a reference period and a monitoring period; using digital filtering to isolate from the EMG signals spectral data for a plurality of frequencies bands selected from the range of about 2 Hz to about 1000 Hz; calculating a first PCA value, the first PCA value being determined from spectral data for the plurality of frequency ranges from at least one part of the reference period; calculating a second PCA value, the second PCA value being determined from spectral data for the plurality of frequency ranges from at least one part of the monitoring period; comparing the second PCA value to the first PA value; and determining whether to trigger an alarm condition using said comparison of the first PCA value to the second PCA value.

A method of detecting seizures with motor manifestations comprising including detecting EMG signals; using digital filtering to isolate from said EMG signals spectral data for a plurality of frequency bands selected from the range of about 2 Hz to about 1000 Hz; calculating a first T-squared value from the spectral data; comparing said first T-squared value to a threshold T-squared value; and determining whether to trigger an alarm condition using said comparison of the first T-squared value to the threshold T-squared value.

An apparatus for detecting seizures with motor manifestations, the apparatus comprising one or more EMG electrodes capable of providing an EMG signal substantially representing seizure-related muscle activity; and a processor configured to receive the EMG signal, process the EMG signal to determine whether a seizure may be occurring, and generate an alert if a seizure is determined to be occurring based on the EMG signal; wherein the processor is capable of processing the EMG signal to determine whether a seizure may be occurring by calculating a T-squared statistical value or a PCA statistical value.

BRIEF DESCRIPTION OF THE DRAWINGS

FIGS. 9A-D illustrate one embodiment of a user interface that may let a user to adjust various settings.

DETAILED DESCRIPTION

Figure 1:
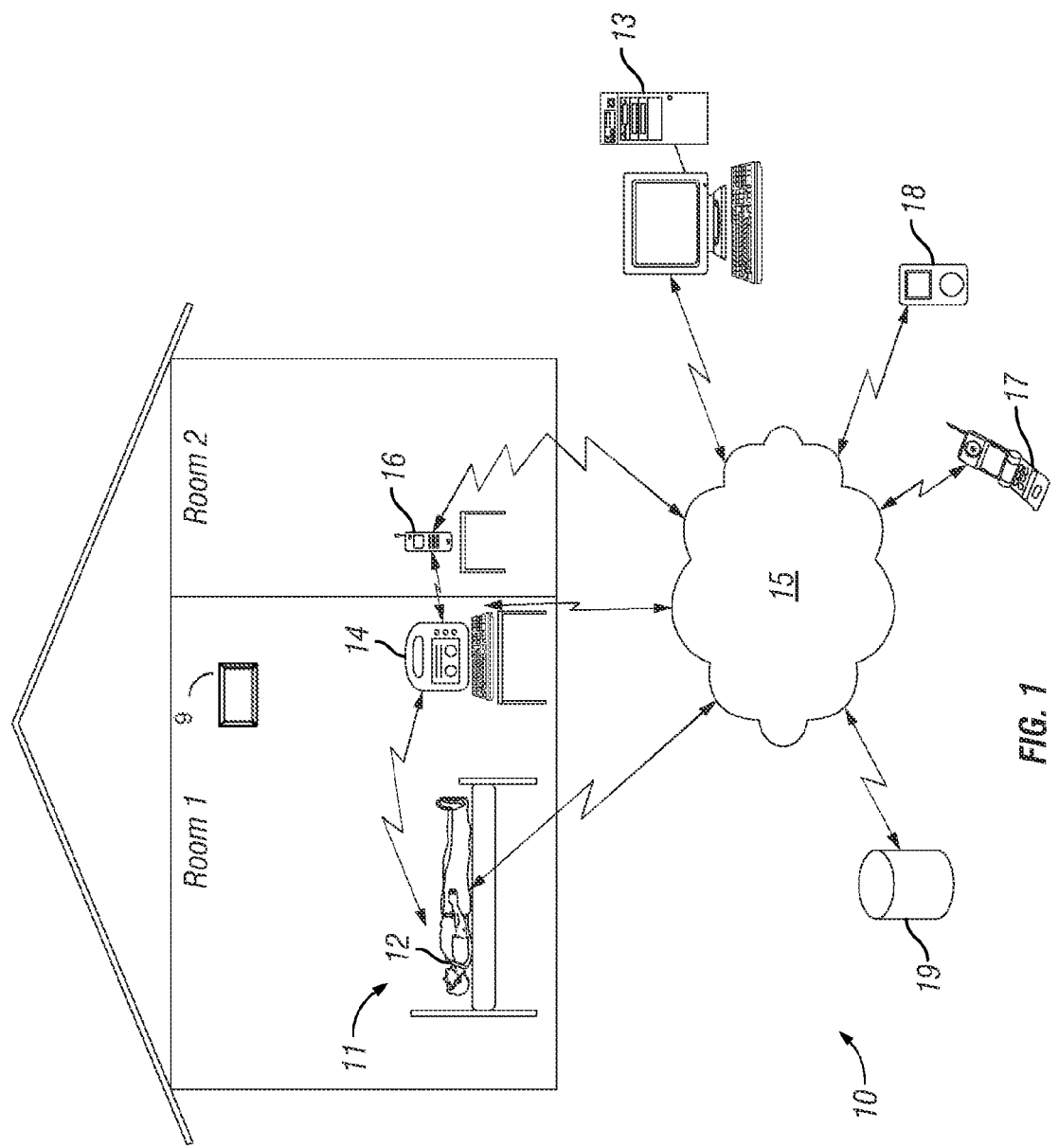
FIG. 1 illustrates one embodiment of a seizure detection system.

In some embodiments, an apparatus for detecting seizures with motor manifestations may comprise one or more EMG electrodes capable of providing an EMG signal substantially representing seizure-related muscle activity, and a processor configured to receive the EMG signal, process the EMG signal to determine whether a seizure may be occurring, and generate an alert if a seizure is determined to be occurring based on the EMG signal.

In some embodiments, an apparatus for detecting seizures with motor manifestations may comprise a detection unit which includes EMG electrodes and a base unit in communication and physically separated from said detection unit, wherein the base station is configured for receiving and processing EMG signals from the detection unit, determining from the processed EMG signals whether a seizure may have occurred, and sending an alert to at least one caregiver. In some embodiments, the base station may separately process the data provided by the detection unit for verification of the alarm condition. If the base station agrees with the alarm, then the base station may generate an alarm to remote devices and local sound generators. Having the base station agree to the detection unit's alarm introduces a voting concept. Both devices may vote on the decision and agree to sound the alarm. This may be used to limit false alarms.

In some embodiments, EMG signals may be collected for a time period and processed by filtering to select a plurality of frequency bands. For example, an EMG frequency spectrum may be broken up into a number of frequency bands, such as three or more, and one or more characteristics of each frequency band, for example, power content of the band or spectral density at one or more frequencies within the band, may be measured. The "power content" or "power amplitude" of the band may relate to muscle work that may be achieved over a given period of time and may be related to the spectral density (e.g., power per frequency) integrated over a given frequency range. In general, the power content or spectral density may be measured as a value that is proportional to the actual power content or spectral density, e.g., when adjusted by some factor. A measured characteristic for a frequency band may be normalized by its variance and covariance with respect to the characteristic as measured in other frequency bands and the resulting normalized values processed to determine Hotelling's T-squared statistics. Based on the T-squared statistical analysis the EMG signals may be used to assess whether a seizure incident is declared and whether an alarm is sent to one or more locations.

In some embodiments, calculation of a T-squared statistical value may include an assignment of weighting factors to the signals from different frequency bands. Weighting factors may, for example, be determined by analyzing signals associated with the various frequency bands obtained during a training period. The weight assigned to each of the frequency bands may, for example, be calculated from the inverse of the variance/covariance matrix of the frequency band calculated during the training period. In this approach, a frequency band exhibiting more muscle activity (usually a lower frequency range) may be assigned less weight than a frequency band exhibiting lesser muscle activity (usually a higher frequency range). Weighting factors may also be assigned such that signals from a frequency band that exhibits large muscle activity during normal activity is lessened such as to minimize the probability that a false alarm is initiated and/or to improve discrimination between normal activity and seizure episodes. Appropriate weighting may depend upon an individual's normal muscle movement observed during a training period. For some individuals, the T-squared calculation may essentially assign equal weight to the signals from the three frequency bands and for other individuals the weighting factors may be different, such as to increase the sensitivity of the technique for detection of seizure activity.

In some embodiments, multiple frequency bands may be analyzed using Principal Components Analysis ("PCA"). For example, three frequency bands may be selected for each EMG signal, and up to that many, such as three, principal components may be used. The width of these bands may vary, with some being narrower and others wider. In some embodiments, statistical parameters based on PCA analysis may be compared to a reference value, such as a baseline PCA value determined during a training period.

In some embodiments, EMG output may be compared to general seizure characteristics and to one or more threshold values. If one or more values of the EMG output data exceeds one or more thresholds an event may be logged, such as by logging the event in a register. For example, EMG output may be used to calculate a T-squared statistical value which may be compared to a T-squared threshold value and used to log detected events in a register. By way of further example, events logged in one or more registers may also correspond to the presence of a characteristic GTC waveform, the presence of data bursts, or to other characteristics such as further described in U.S. application Ser. No. 13/275,309. Analysis of events logged in registers for various characteristics of the output data may be used to assess whether a seizure incident is declared and whether an alarm may be sent to one or more locations.

In some embodiments, methods and/or apparatuses described herein may be customized for an individual or for a patient demographic. For example, in some embodiments, an apparatus may establish or adjust sensitivity settings based upon a Maximum Voluntary Contraction (MVC) of muscles for an individual. MVC is related to the maximum force a patient may apply during a voluntary contraction. The strength of muscles may vary from individual to individual and the amplitude of the EMG signal may also vary. Measurement of electromyographic data for a patient during maximum voluntary muscle exertion (and adjusting sensitivity settings accordingly) may customize the technique to an individual's musculature and may enhance the selectivity of methods described herein for discrimination of seizure activity versus data from a non seizure period. In some embodiments, a T-squared threshold value may be set based upon a T-squared statistical value calculated from EMG data obtained while the individual is at rest and while an individual is undergoing the MVC. In some embodiments, a threshold T-squared statistical value may be a value that is greater that the T-squared statistical value at rest by some factor of the difference between T-squared statistical values calculated during MVC and while the individual is at rest. In some embodiments, the threshold Z-factor may be scaled based upon eletromyographic data obtained while the patient is executing the MVC.

In some embodiments, seizure detection methods and/or apparatuses as described herein may be adaptive. For example, during or after a seizure event, a human operator may review and adjust the settings of various factors (those factors further described herein), such as the threshold Z-factor, alarm lag factor, or weighting factors (for signal from a plurality of selected frequency bands), based upon the severity of the seizure, the non-detection of an actual seizure, or a false detection. In some embodiments, detection settings may change automatically, such as based on the presence of any number of false positive events. For example, if an alarm is triggered an individual may be given the option to cancel the alarm. The system may automatically categorize the event as a false positive and may be configured to adjust a detection factor, such as, for example, the threshold Z-factor and/or alarm lag, to minimize future false positive event characterizations. As seizure data is collected from one or more patients the settings used to monitor a given patient or patient demographic may change to better predict future seizures. For example, detection algorithms may include or use an adjustable template file that comprises various settings and which may be updated based on the success of the method. The association between collected data and seizure related incidents, e.g., declared events, actual seizures and inaccurately reported incidents, may be tracked to evaluate the methods success.

In some embodiments, a method and apparatus may be used, for example, to initiate an alarm protocol, create a log of seizure incidents to help medically or surgically manage the patient, activate a Vagal Nerve Stimulator, or activate other stimulating devices that may be used to abort or attenuate a seizure. In some embodiments, a log of seizure related incidents may prompt a physician to understand more quickly the failure of a treatment regimen.

The apparatuses and methods described herein may be used to detect seizures and timely alert caregivers of a seizure using EMG, among other things. The apparatuses and method may be used, for example, to initiate an alarm protocol, create a log of seizure incidents to help medically or surgically manage the patient, activate a Vagal Nerve Stimulator, or activate other stimulating devices that may be used to abort or attenuate a seizure. In some embodiments, a log of seizure related incidents may prompt a physician to understand more quickly the failure of a treatment regimen. The apparatuses and methods may comprise a process or processes and device and/or system of devices for detecting seizures with motor manifestations including, but not limited to Tonic-Clonic, Tonic-only, or Clonic-only seizures. A "motor manifestation" may in some embodiments generally refer to muscle activity, whether sustained or otherwise. A motor manifestation may or may not result in overt movement of an individual's body.

A variety of systems may be suitably used for collecting large amounts of EMG and other patient-related data, prioritizing data for storage, organizing such data for system optimization, and/or initiating an alarm in response to a suspected seizure. FIG. 1 illustrates an exemplary embodiment of such a system. In the embodiment of FIG. 1, a seizure detection system 10 may include a detection unit 12, an optional base station 14, an optional video camera 9 and an optional alert transceiver 16. The detection unit may comprise one or more EMG electrodes capable of detecting electrical signals from muscles at or near the skin surface of a patient, and delivering those electrical EMG signals to a processor for processing. The base station may comprise a computer capable of receiving and processing EMG signals from the detection unit, determining from the processed EMG signals whether a seizure may have occurred, and sending an alert to a caregiver. An alert transceiver may be carried by, or placed near, a caregiver to receive and relay alerts transmitted by the base station.

In using the apparatus of FIG. 1, a person 11 susceptible to epileptic seizures may be resting in bed or may be at some other location as daily living may include, and may have a detection unit 12 in physical contact with or in proximity to his or her body. The detection unit 12 may be a wireless device so that a person may be able to get up, walk around, and engage in daily activities without having to be tethered to an immobile power source or to a bulkier base station 14. For example, the detection unit 12 may be woven into a shirt sleeve, or may be mounted to an armband or bracelet. In other embodiments, one or more detection units 12 may be placed or built into a bed, a chair, an infant car seat, or other suitable clothing, furniture, equipment and accessories used by those susceptible to seizures. The detection unit 12 may comprise a simple sensor, such as an electrode, that may send signals to the base station for processing and analysis, or may comprise a "smart" sensor having some data processing and storage capability. In some embodiments, a simple sensor may be connected via wire or wirelessly to a battery-operated transceiver mounted on a belt worn by the person.

The system may monitor the patient, for example, while resting, such as during the evening and nighttime hours or while engaged in some other activity. If the detection unit 12 on the patient detects a seizure, the detection unit 12 may communicate wire or wirelessly, e.g., via a communications network or wireless link, with the base station 14, to a remote cell phone or other hand held device via bluetooth or simultaneously to a base station and remote cell phone. The detection unit 12 may send some signals to the base station device for more thorough analysis. For example, the detection unit 12 may process and use EMG signals (and optionally ECG and temperature sensor signals) to make an initial assessment regarding the likelihood of occurrence of a seizure, and may send those signals and its assessment to the base station 14 for separate processing and confirmation. If the base station 14 confirms that a seizure is likely occurring, then the base station 14 may initiate an alarm for transmission over the network 15 to alert a caregiver by way of email, text, or any suitable wired or wireless messaging indicator. In some embodiments, if one or more of the detection unit 12, the base station 14, or a caregiver, e.g., a remotely located caregiver monitoring signals provided from the base station, determines that a seizure may be occurring a video camera 9 may be triggered to collect information. In some embodiments, a cell phone or other hand held device may be configured with an application that enables more thorough analysis than the analysis performed by the detection unit 12. Thus, a cell phone may, e.g., serve some of the same or similar functions as a base station.

The base station 14, which may be powered by a typical household power supply and contain a battery for backup, may have more processing, transmission and analysis power available for its operation than the detection unit 12, may be able to store a greater quantity of signal history, and evaluate a received signal against that greater amount of data. The base station 14 may communicate with an alert transceiver 16 located remotely from the base station 14, such as in the bedroom of a family member, or to a wireless device 17, 18 carried by a caregiver or located at a work office or clinic. The base station 14 and/or transceiver 16 may send alerts or messages to caregivers, or medical personnel via any suitable means, such as through a network 15 to a cell phone 17, PDA 18 or other client device. The system 10 may thus provide an accurate log of seizures, which may allow a patient's physician to understand more quickly the success or failure of a treatment regimen. Of course, the base station 14 may simply comprise a computer having installed a program capable of receiving, processing and analyzing signals as described herein, and capable of transmitting an alert. In other embodiments, the system 10 may simply comprise, for example, EMG electrodes and a smartphone, such as an iPhone, configured to receive EMG signals from the electrodes for processing the EMG signals as described herein using an installed program application. In further embodiments, so-called "cloud" computing and storage may be used via network 15 for storing and processing the EMG signals and related data. In yet other embodiments, one or more EMG electrodes could be packaged together as a single unit with a processor capable of processing EMG signals as disclosed herein and sending an alert over a network. In other words, the apparatus may comprise a single item of manufacture that may be placed on a patient and that does not require a base station separate transceiver. In some embodiments, an alarm may cause the cell phone to dial out to a predetermined phone number with, e.g., a test message and may be used to open a voice comm link.

In the embodiment of FIG. 1, the signal data may be sent to a remote database 19 for storage. In some embodiments, signal data may be sent from a plurality of epileptic patients to a central database 19 and "anonymized" to provide a basis for establishing and refining generalized "baseline" sensitivity levels and signal characteristics of an epileptic seizure. The database 19 and base station 14 may be remotely accessed via network 15 by a remote computer 13 to allow updating of detector unit and/or base station software, and data transmission. The base station 14 may generate an audible alarm, as may a remote transceiver 16. All wireless links may be two-way for software and data transmission and message delivery confirmation. The base station 14 may also employ one or all of the messaging methods listed above for seizure notification. The base station 14 may provide an "alert cancel" button to terminate the incident warning.

In some embodiments, a transceiver may additionally be mounted within a unit of furniture or some other structure, e.g., an environmental unit or object. If a detection unit is sufficiently close to that transceiver, such a transceiver may be capable of sending a signal to a base station. Thus, the base station may be aware that information is being received from that transceiver, and therefore the associated environmental unit. In some embodiments, a base station may select a specific template file or use associated device settings, including, for example, threshold Z-factor, weighting coefficients, alarm lag settings, and/or other settings as described further herein, in a manner that may be dependent upon whether or not it is receiving a signal from a certain transceiver. Thus, for example, if the base station receives information from a detector and from a transceiver that is associated with a bed or crib it may treat the data differently than if the data is received from a transceiver associated with another environmental unit, such as, for example, a unit attached to a restroom sink or clothing typically worn while an individual may be exercising. Moreover, the detection unit and base station may have input output capability and, in some embodiments, adjustment of settings on one unit may result in corresponding adjustment of setting in the other.

The embodiment of FIG. 1 may be configured to be minimally intrusive to use while sleeping or minimally interfere in daily activities, may require a minimum of electrodes such as one or two, may require no electrodes to the head, may detect a seizure with motor manifestations, may alert one or more local and/or remote sites of the presence of a seizure, and may be inexpensive enough for home use.

Figure 2:
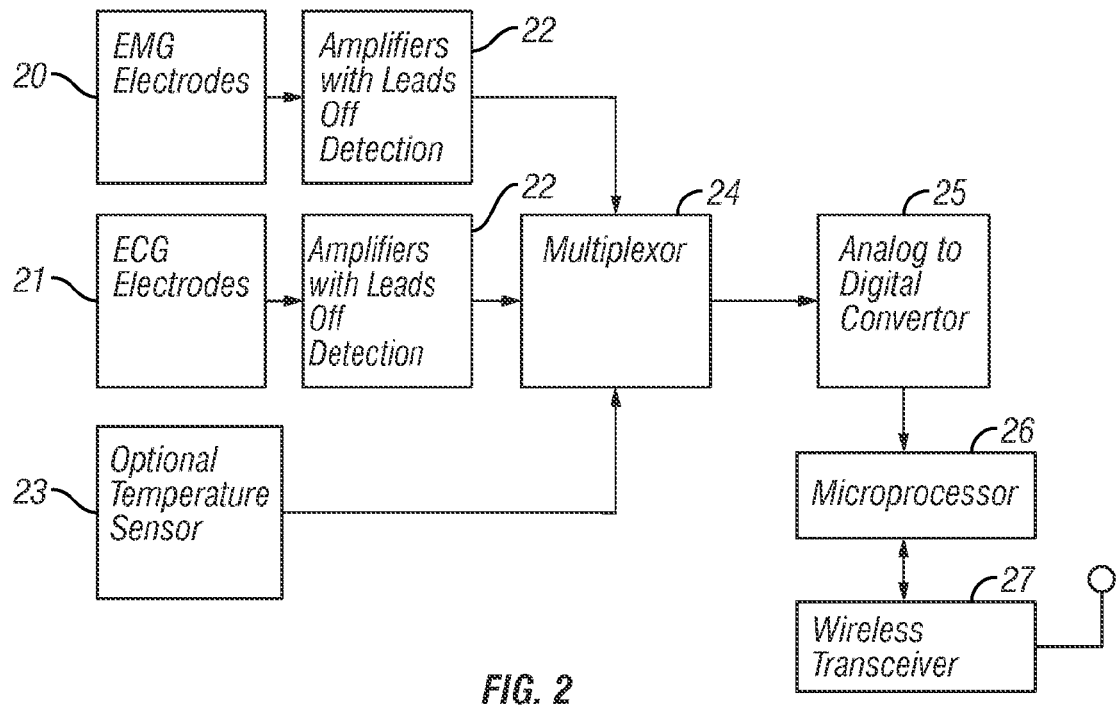
FIG. 2 illustrates one embodiment of a detection unit and base station for a seizure detection system.

FIG. 2 illustrates an embodiment of a detection unit 12 or detector. The detection unit 12 may include EMG electrodes 20, and may also include ECG electrodes 21. The detection unit 12 may further include amplifiers with leads-off detectors 22. In some embodiments, one or more leads-off detectors may provide signals that indicate whether the electrodes are in physical contact with the person's body, or otherwise too far from the person's body to detect muscle activity, temperature, brain activity or other patient phenomena.

The detection unit 12 may further include a temperature sensor 23 to sense the person's temperature. Other sensors (not shown) may be included in the detection unit, as well, such as accelerometers. Signals from electrodes 20 and 21, temperature sensor 23 and other sensors may be provided to a multiplexor 24. The multiplexor 24 may be part of the detection unit 12 or may be part of the base station 14 if the detection unit 12 is not a smart sensor. The signals may then be communicated from the multiplexor 24 to one or more analog-to-digital converters 25. The analog-to-digital converters may be part of the detection unit 12 or may be part of the base station 14. The signals may then be communicated to one or more microprocessors 26 for processing and analysis as disclosed herein. The microprocessors 26 may be part of the detection unit 12 or may be part of the base station 14. The detection unit 12 and/or base station 14 may further include memory of suitable capacity. The microprocessor 26 may communicate signal data and other information using a transceiver 27. Communication by and among the components of the detection unit 12 and/or base station 14 may be via wired or wireless communication. In some embodiments, the detection unit 12 may be equipped with audio recording capability and may be configured for sending an audio signal in addition to other transmitted data.

Of course, the exemplary detection unit of FIG. 2 may be configured differently. Many of the components of the detector of FIG. 2 may be base station 14 rather than in the detection unit 12. For example, the detection unit may simply comprise an EMG electrode 20 in wireless communication with a base station 14. In such an embodiment, A-D conversion and signal processing may occur at the base station 14. If an ECG electrode 21 is included, then multiplexing may also occur at the base station 14.

In another example, the detection unit 12 of FIG. 2 may comprise an electrode portion having one or more of the EMG electrode 20, ECG electrode 21 and temperature sensor 23, in wired or wireless communication with a small belt-worn transceiver portion. The transceiver portion may include a multiplexor 24, an A-D converter 25, microprocessor 26, transceiver 27 and other components, such as memory and I/O devices (e.g., alarm cancel buttons and visual display).

Figure 3:
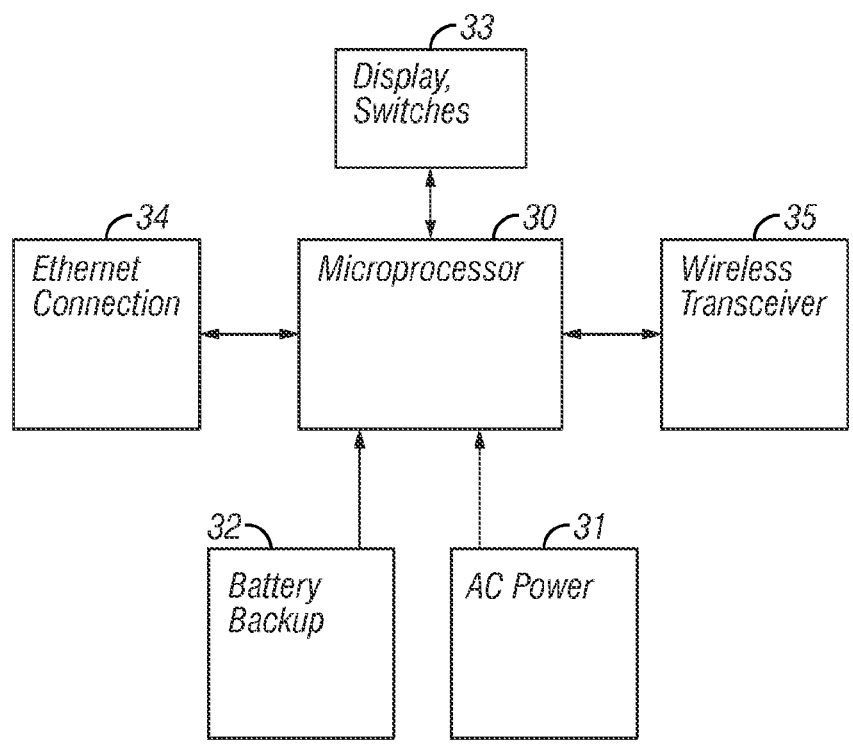
FIG. 3 illustrates one embodiment of a base station.

FIG. 3 illustrates an embodiment of a base station 14 that may include one or more microprocessors 30, a power source 31, a backup power source 32, one or more I/O devices 33, and various communications means, such as an Ethernet connection 34 and transceiver 35. The base station 14 may have more processing and storage capability than the detection unit 12, and may include a larger electronic display for displaying EMG signal graphs for a caregiver to review EMG signals in real-time as they are received from the detection unit 12 or historical EMG signals from memory. The base station 14 may process EMG signals and other data received from the detection unit 12. If the base station 14 determines that a seizure is likely occurring, it may send an alert to a caregiver via transceiver 35. In some embodiments, the base station 14 may be equipped to receive a signal including audio data (such as from a detection unit 12), may be equipped audio recording capability or both. The base station may also be configured for sending audio data to a caregiver in addition to other transmitted data.

Various devices in the apparatus of FIGS. 1-3 may communicate with each other via wired or wireless communication. The system 10 may comprise a client-server or other architecture, and may allow communication via network 15. Of course, the system 10 may comprise more than one server and/or client. In other embodiments, the system 10 may comprise other types of network architecture, such as a peer-to-peer architecture, or any combination or hybrid thereof.

A normal voluntary muscle movement may comprise a coordinated contraction of agonist and antagonistic muscles in a cooperative way to achieve a particular motion. Often during seizures, such coordination is lost. Instead, the muscles may tend to lock up different parts of the body with muscles fighting each other. A good example of this scenario may be seen in the tonic phase of a motor seizure when the biceps and triceps muscles are both stimulated. These muscles may fight each other with very high amplitude signals, but the arms may not move very much at all. This higher frequency electrical activity may, for example, be characteristic of a Generalized Tonic-Clonic (GTC) seizure or generalized tonic seizure. Thus, motor manifestations (and high-amplitude EMG signals) may be present without overt signs of movement. As noted previously, seizures that exhibit such characteristics may not be consistently detected with accelerometer-based detectors. The EMG electrodes described herein may detect the motor manifestations of a patient (even where overt signs of muscle activity are absent), and may generate EMG signals suitable for processing and analysis according to a variety of methods.

EMG electrodes may be placed on or near one or more muscles, such as the biceps. Alternatively, one EMG detector may be placed over a biceps muscle and one EMG detector placed over a triceps muscle on the same arm using an elastic arm band, clothing, tape or some other method of maintaining the electrodes in contact over those muscles. If the one or more muscles that are monitored include an agonist and antagonist muscle pair, the relation of EMG data between the muscles and whether such data may be correlated as might be expected in coordinated movement, may be used to distinguish normal muscle behavior from motor manifestations associated with a seizure. As a seizure begins, the amplitude of the signals from the EMG electrodes may begin to increase until the amplitude is quite high. However, high amplitude signals may not necessarily characterize a real seizure. Many body movements, including night terrors, may also result in high amplitude signals. Therefore, merely detecting high amplitude signals may not result in seizure detection. High amplitude signals sustained for a somewhat longer period of time may provide a better indication of a seizure.

To better characterize normal and seizure-related muscle activity monitoring as described herein may involve not only observing changes in EMG signal amplitude, techniques herein may further evaluate the variance/covariance of power amplitudes for selected frequency bands, and use such data to calculate a T-squared statistical value. Observing changes in signals from the selected spectral bands (and, for example, normalization of signals from the spectral bands based on variance/covariance matrices—such as using an inverse matrix determined there from may assist in differentiating between actual seizures and events such as night terrors that, if monitored, otherwise may be challenging to tell apart. The magnitude of T-squared statistical values may, e.g., reflect a condition wherein the distribution of signals across different frequency bands has changed. For example, when certain high frequency signals grow in relative amplitude to other frequency ranges a calculated T-squared statistical value may change in a highly sensitive manner. Moreover, in some situations, T-squared values may change even if the total power has not significantly changed.

A number of noise sources such as 1/f and some environmental sources may increase the overall power and overall positive amplitude of EMG data but may be readily distinguished from EMG signal originating from a seizure using the techniques described herein. For example, some sources of noise comprise signals from different frequency bands that may change in characteristic ways and the system may be programmed or adapted to distinguish such changes from those associated with an actual seizure. Moreover, during a seizure, high frequency components may show large variance/covariance with other regions of an EMG spectrum. Measurement of variances/covariances (and T-squared statistical values calculated thereof) and/or adjustment of weights associated with bands may therefore serve as a tool to augment differences between EMG signals originating from various sources, including, e.g., a seizure, normal muscle movement and various sources of noise (such as in particular those that are frequency dependent), thereby facilitating characterization and detection of such events.

In the normal recruitment of muscle activity in voluntary contractions, low frequency signals (about 30 Hz) may be sent to recruit muscles, and later, as the activity becomes more intense, higher frequency signals may be sent to maintain the muscle contraction. Such signals may be as high as 300 Hz-400 Hz, although signals sent in trained athletes may be up to about 1,000 Hz. The electrical frequencies recorded with macro-electrodes may frequently extend above 300 Hz in a sustained manner during a seizure with motor manifestations. However, above about 300 Hz-400 Hz, the signal may generally be considerably weaker. Even though high frequency signals may be relatively weak and high frequency signal amplitudes may contribute a small fraction of the total power, for some individuals, the presence of such high frequency signals and/or changes in signal ratio between high frequency ranges and other frequency ranges may be highly indicative of a seizure. Such changes may be captured, as described herein, by analysis of variances/covariances within and between frequency bands, information that may be lost without partitioning of frequency data in different bands and use of T-squared statistical methods.

In some embodiments, relative changes in signals derived from various frequency components for an individual undergoing normal muscle activity may be tracked and compared to changes in frequency components for that individual as that individual experiences a seizure. Weighting factors associated with the measured power in various frequency bands may be adjusted to distinguish between typical normal muscle movement, sources of noise, and seizure activity. In some embodiments, variables including, e.g., threshold Z-values, lag settings, weighting factors associated with one or more frequency band or combinations thereof, may be adjusted to distinguish between typical normal muscle movement, sources of noise, and seizure activity.

A seizure-prone individual may, in some embodiments, be monitored by collecting EMG data during a monitoring period, calculation of statistical values, and comparison of those values to reference EMG data or values collected during one or more reference periods. A reference period may include monitoring an individual in a supervised setting, such as during a period with independent verification (such as with video monitoring) of any seizures that may occur. A reference period may be the first time an individual wears a device. However, a reference period may be also be repeated, such as if deemed necessary, or may be performed at other times, such as after an individual has become accustomed to wearing the device.

During a reference period, an individual may be monitored while engaged in various activities. For example, in some embodiments, a reference period may include collection of EMG data while the individual is at rest, executing common daily activities, executing activities which may typically involve vigorous and/or repetitive motion (such as, by way of nonlimiting example, the execution of a maximum voluntary contraction), or any combinations thereof. EMG data collected while executing different activities may be used to characterize resting and/or elevated portions of muscle activity that may be experienced by a patient and which may be distinguished over seizure activity. Such activity may be used to characterize baseline activity that may, in some embodiments, be used to establish a reference T-squared value to which T-squared values in a monitoring period are compared, such as by calculation of a difference between those T-squared values. In some embodiments, a method may, periodically re-normalize EMG data collected in a monitoring period by executing either or both of an electrode re-normalization and a training period (with recalculation of a variance/covariance matrix, such as by determining an inverse matrix, and establishment of a set of weighting coefficients) as part of reference period(s) that are repeated during daily use. Re-normalization may effectively re-center muscle activity around a T-squared baseline that provides a small T-squared value and this small value may be used as a reference T-squared baseline from which T-squared values are compared, such as by subtraction of those values or by calculation of a delta value between them. In some embodiments, a reference T-squared value may be rounded to zero and/or dropped from the calculation. Thus, in some embodiments, a T-squared value obtained during monitoring may be used (without subtraction each time by a reference value each time that value is calculated). This may be considered comparing the T-squared value during monitoring to a value of zero. Periodic sampling of the electrodes during monitoring may, in some embodiments, be used to verify that a reference T-squared value during times after a normalization remains low, and that the comparison of a monitoring T-squared value to a number that is small (or zero) does not result in incorrect analysis of muscle activity.

EMG data obtained during a reference period may be used to calculate a variance/covariance matrix and/or inverse matrix for the T-squared statistic at a time when a patient is not undergoing a seizure event, and may, in some embodiments, also be used to establish a baseline or reference T-squared statistical value. For example, during a reference period, the apparatus may self-train for an individual by calculating the variance/covariance matrix for the T-squared statistic using EMG data obtained when an individual is initially connected. Calculating the T-squared statistic across selected frequency bands during a non-seizure-resting period may provide a baseline value against which subsequent signals are analyzed. Calculating the variance/covariance matrix for the T-squared statistic across selected frequency bands during a non-seizure-resting period may be used to establish weighting coefficients that may be used in subsequent calculations of T-squared statistical values. In some embodiments, an inverse matrix may be calculated and weights assigned to each of a plurality of selected frequency bands may be determined from the coefficients of the inversion matrix. The inverse matrix of the variance/covariance matrix may be a matrix (which may also be referred to as a reciprocal matrix) that, when convoluted with the variance/covariance matrix, produces the identity matrix. Use of the inversion matrix to establish weights and normalize T-squared values has been found to be a way to automatically adjust the contribution of different frequency bands to a patient's musculature.

In some embodiments, a reference period (or periods) may be used to establish device settings, such as, e.g., the threshold Z-factor or threshold T-squared value, weighting factors between frequency regions, alarm lag settings, the variance/covariance matrix for the reference T-squared statistic, standard deviation of the reference T-squared statistic, other factors, or any combinations thereof. Future periods of use (monitoring periods) may involve electrode normalization (such as involving adjustment of amplifier and/or digital signal gain settings); however, other device settings (such as noted above) may, at least in some embodiments, not be subject to change—the predetermined values of those constants (determined from one or more reference periods) may be held constant and used for the entirety of the monitoring period. For example, after determination of device settings in the one or more reference periods, monitoring an individual for seizure activity may, in some embodiments, involve normalization of electrodes, collection of EMG data with calculation of a T-squared value, comparison of that data with a predetermined threshold T-squared value, and evaluation of whether an alarm may be initiated. A predetermined threshold T-squared value may, in some embodiments, involve collection of a T-squared reference baseline (during a reference period) and setting the threshold T-squared value to be some number of standard deviation units of the collected T-squared reference baseline. A predetermined threshold T-squared value may, in some embodiments, involve collection of a T-squared value (during a reference period while the patient is executing an MVC) and setting the threshold T-squared value to be a certain factor of the T-squared value obtained while executing the MVC. A predetermined threshold T-squared value may, in some embodiments, involve collection of a T-squared value (during a reference period and while executing an MVC), repeating the calculation of a T-squared value MVC several times, calculating a standard deviation for the several repetitive T-squared calculations performed during the MVC, and scaling the threshold T-squared value to be some number of the calculated standard deviation from the repetitive T-squared values obtained during the MVC. In some embodiments, after determination of device settings in the one or more reference periods, monitoring an individual for seizure activity may, in some embodiments, involve normalization of electrodes, collection of EMG data with calculation of a T-squared value, comparison of that data with a reference T-squared value and evaluation of whether an alarm may be initiated.

In some embodiments, comparison of T-squared values (e.g., comparison of a T-squared value determined during a monitoring period and a reference T-squared value) and evaluation of whether to initiate an alarm may involve scaling the difference between T-squared values in units of standard deviations of the reference T-squared statistic and assessment of whether the number of standard deviations exceeds a threshold Z-factor (in units of standard deviations) or exceeds that factor for a certain time interval. A threshold T-squared value may exceed a reference T-squared value by some value, such as a certain number of standard deviations (and may be referred to as a threshold Z-factor) or may be scaled in some other way—such as using an MVC calculation described above or set to be an acceptable value that has been determined to work for all patients of a certain demographic (such as patients with a certain mid upper arm circumference).

In some embodiments, a reference period or periods may be used to establish device settings, and monitoring periods may use those settings. A monitoring period may involve electrode normalization (such as involving adjustment of amplifier and/or digital signal gain settings), but otherwise use device settings predetermined in the reference periods. In some embodiments, a reference period may additionally or alternatively be executed during the same period of time, for example, on the same day or interval, that the system is monitoring a patient. Such a reference period may be conducted at an individual's home. For example, in some embodiments, an apparatus may be configured to initiate an automatic calibration (such as may involve adjustment of electrode gain settings) and the apparatus may be normalized to account for, e.g., how tightly the EMG sensors are placed over a muscle, humidity, EMG sensor location, or other factors. Normalization may, in some embodiments, include re-training the system by collection of data for a period of time as necessary to recalculate the variance/covariance matrix for T-squared statistical calculations and setting of weighting factors, or both. Normalization may, in some embodiments, include calibration of electrodes (such as including adjustment of gain settings and/or establishing that a common mode rejection between detector inputs is within an acceptable and/or expected range) and system training with the collection of data for calculation of a reference T-squared statistical value, the collection of data for calculation of weighting factors between selected bands, or both. Upon collection of data during normalization, the system may establish a reference T-squared statistical value, may replace a default reference T-squared statistical value, or replace a previously used reference T-squared value. For example, the system may substitute the newly determined reference T-squared value for one determined. During a re-training period, the system may, in some embodiments, also be monitoring the patient for seizure activity. For example, during the collection of data for training, the system may compare the data, i.e., as collected in real-time, to reference values, such as may have been established from a previous training period or patient demographic, and evaluate whether a seizure may be occurring. As a system completes monitoring within a given time period, the system may incorporate data from that time period into settings for evaluation of a subsequent period. The system may, in some embodiments, evaluate the data collected during normalization and only incorporate the recently collected data (and update settings) if the data meets certain requirements. For example, updating a given setting may depend upon whether the value of the reference T-squared value, standard deviation of the reference T-squared baseline or both are within accepted boundaries. The system may also execute a routine wherein spurious data, e.g., data outliers—such as from random noise or inadvertent rapid movements of the individual may be removed. Normalization may occur at regular intervals or in response to a certain criteria. The system may, for example, automatically re-train the system by collecting EMG data from a time period when an individual is initially connected to the device or when a sufficient increase or decrease in the average amplitude of a signal occurs or occurs over a certain time period.

Thus, different embodiments may incorporate settings from either a reference period that is conducted in a supervised setting, during periodic normalization (such as including periodic normalization in home use), or both. In addition, in some embodiments, at least some device settings may be established based on data derived from all patients or from patients of a certain demographic. For example, as an alternative to monitoring of an individual during a reference period in a supervised setting, an individual may use a device which has been programmed with settings that are specific for all patients or for patients of a certain demographic. By way of non-limiting, as an alternative to setting a threshold T-squared value or threshold Z-factor based on MVC or scaling in terms of the standard deviation of a reference period those settings may be set based on typical settings that have been shown to work for patients with a given mid upper arm circumference (MUAC), such as by using one threshold setting for individuals with MUAC values of about 16 cm to about 24 cm and a different setting for individuals with MUAC values of about 24 cm to about 28 cm. In some embodiments, an individual may wear a device and, upon initial monitoring, the EMG electrodes may execute a calibration routine (such as involving adjustment of amplifier and/or digital signal gain settings); however, other device settings, such as, for example, reference T-squared statistic, threshold Z-factor, and alarm lag settings, may be population specific. In other embodiments, the reference T-squared statistic may be automatically determined upon initially connecting the device, such as, for example, along with calibration and during training, and therefore may be customized to the individual. However, other device settings such as the threshold Z-factor and alarm lag settings may be population specific. Thus, some of the aforementioned approaches may facilitate monitoring of a patient without the need for a patient to spend time in a supervised setting.

In some embodiments, device settings may be adjustable only upon external verification and review by a human operator. In other embodiments, adjustment of device settings may alternatively or additionally be executed automatically. For example, as previously noted, if an alarm is triggered, an individual may be given the option to cancel the alarm. In such embodiments, the device may be programmed to log such cancelations as false-positive events. The system may categorize the event as a false positive and the system may be configured to adjust a detection factor, such as, for example, the threshold Z-factor and/or alarm lag, to minimize future false-positive event characterizations. For example, the threshold Z-factor may be increased by an amount, such as about 10 standard deviation units, each time a false-positive event is logged. Alternatively, if the system is scaled in terms of the difference in a reference T-squared baseline and T-squared calculation while executing an MVC, the system may adjust a threshold T-squared value to adjust detection sensitivity.

A device may automatically adjust a setting, such as the threshold Z-factor, each time a false-positive event is logged or the system may only adjust detection setting following a certain number of false-positive event detections. In some embodiments, the system may also include in memory (or access when needed—such as while adjusting setting factors) a record of data from any actual seizures that were correctly identified during previous monitoring periods and/or were detected during a reference period. The system may adjust detection settings and calculate whether the new settings would have resulted in the system missing detection of any previously recorded seizures. Thus, the historical record of detected seizures may serve as a qualifying check to the adjustment of settings. The system may, in some embodiments, adjust settings to find the ideal set point for the various detection settings. For example, either a detection unit or a base station (which, as previously noted, may have more advanced programming capability) may execute an algorithm to find settings that provide optimum selectivity between actual recorded seizures and any events that had been recorded as false positive events. In adjusting settings, the detection system may store or have access to recorded seizures as well as any false-positive events. Moreover, the system (for example, detector unit and/or base station) may store EMG data, that while not sufficient to initiate an alarm, may have been sufficiently close to doing so. The system may then be able to verify that adjustment of settings and use of those settings would not have resulted in a false-positive detection with regard to the stored data. Therefore, the system may have access to the relevant data to dynamically adjust settings to optimize detection of actual seizures and minimize false-positive events and may furthermore do so automatically.

Figure 4:
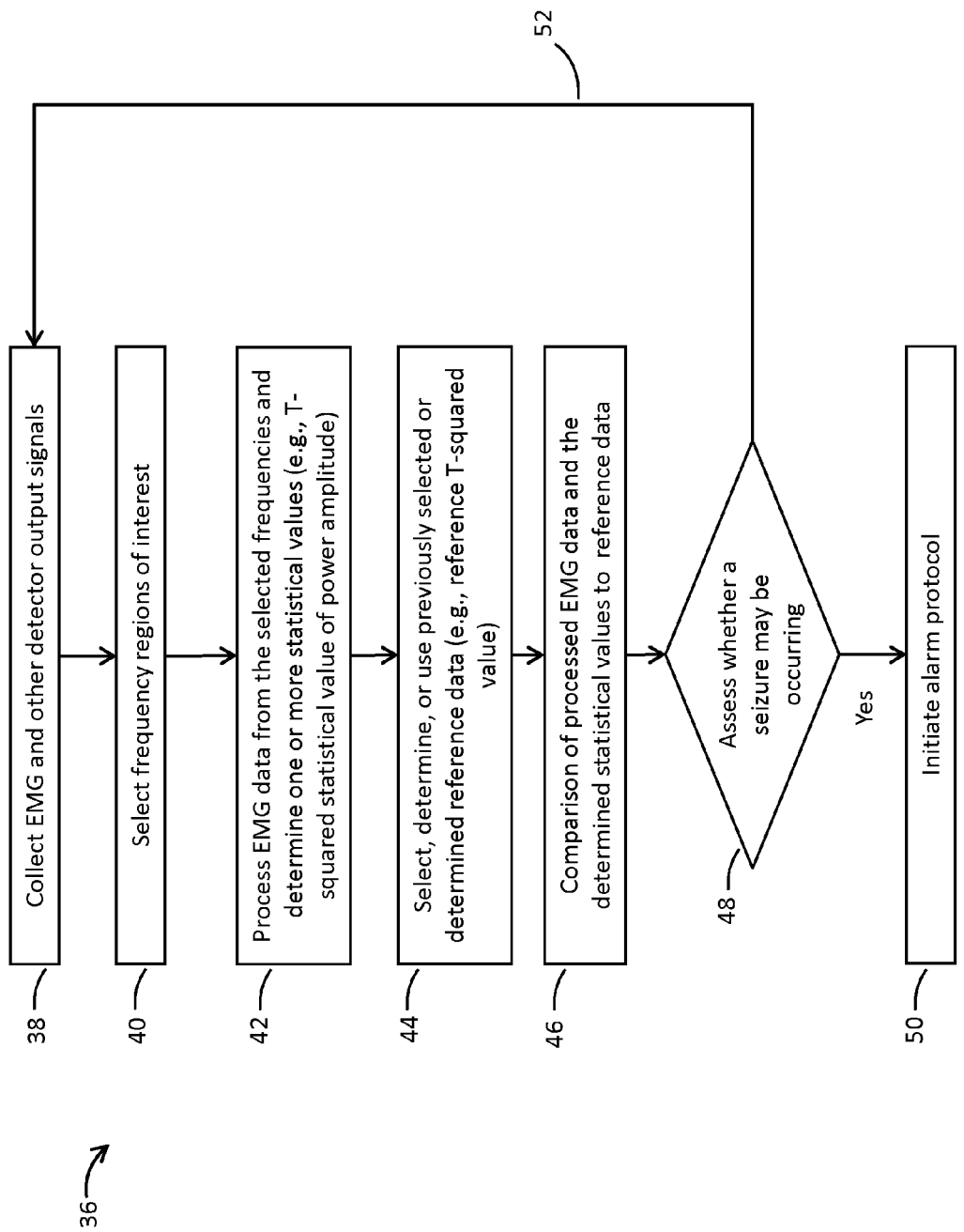
FIG. 4 illustrates one embodiment of a method for monitoring a patient for seizure activity.

FIG. 4 illustrates an exemplary method 36 of monitoring EMG signals for seizure characteristics and initiating an alarm response if a seizure is detected. In a step 38, EMG signals (and optionally other detector output signals) may be collected, such as in an ambulatory or home setting. In a step 40, the EMG signals may be processed by filtering to select a plurality of frequency bands of various widths. Filtering may be accomplished by software or electronic circuit components, such as bandpass filters (e.g., Baxter-King bandpass filters) suitably weighted. For example, in some embodiments, three frequency bands may be selected as follows: Range 1 may range from about 300 Hz to about 400 Hz, Range 2 may range from about 130 Hz to about 240 Hz, and Range 3 may range from about 30 Hz to about 40 Hz. Data from the selected frequency bands may be processed in a step 42 and one or more statistical values may be determined. For example, a T-squared statistical value may be calculated based on the variances/covariances of the power amplitudes in the selected frequency bands. In a step 44 reference data may be determined, selected, or used and the one or more statistical values calculated (step 42) may be compared (step 46) to the reference data. In some embodiments, a T-squared value may be compared to a baseline that is a small number, near zero, or which may be zero because the baseline was adjusted to be so (such as by adjusting weighting coefficients, electrode normalization, or both) based on reference data collected during a reference period. In some embodiments, the difference between a T-squared statistical value and a reference T-squared statistical value (Δ T-squared) may be determined. In a step 48, the method may assess whether a seizure event may be occurring. Such an assessment may, for example, involve scaling Δ T-squared by the number of standard deviations units in which it differs from a reference T-squared baseline, setting a threshold T-squared value based on an MVC, setting a threshold based on a demographic criterion, or setting a threshold using a combination of ways. A scaled value of Δ T-squared, e.g., the Z-factor (in units of standard deviations) may be compared to a threshold Z-factor or threshold T-squared value to determine the likelihood that a seizure may be occurring. Based on the determined likelihood that a seizure may be occurring, the method may initiate an alarm protocol (step 50) and/or the system may collect a next set of EMG data (step 52) and again assess whether to initiate an alarm.

As described in step 38, methods herein involve the collection of EMG data. In some embodiments, detection of seizures may be accomplished exclusively by analysis of EMG electrode data. In other embodiments, a combination of one or more EMG sensors and one or more other sensors may be used. For example, temperature sensors, accelerometers, ECG sensors, other sensors, or any combinations thereof, may be used. Accelerometers may, for example, be placed on a patient's extremities to detect the type of violent movement that may characterize a seizure. Similarly, ECG sensors may be used to detect raised or abnormal heart rates that may characterize a seizure. A monitoring device may detect an epileptic seizure without the customary multitude of wired electrodes attached to the head, as typical with EEG. Combination of EMG with other data may, for example, be used with particularly difficult patients. Patients with an excessive amount of loose skin or high concentrations of adipose tissue, which may affect the stability of contact between an electrode and the skin, may present monitoring challenges and may be candidates for use with multiple sensors. Data from non-EMG sensors (if present) may be used in a number of ways. For example, in some embodiments, the threshold Z-factor or time lag factor may be adjusted based on the presence of data corroborating (or contradicting) that a seizure may be occurring. Thus, the sensitivity of the system to the EMG data may be modified based on corroborating or contradicting evidence from other sensors. In some embodiments, the selection of a specific reference file may, at least in part, be based on data collected by another sensor.

In some embodiments, an EMG detector may comprise a single detection unit such as placed on the biceps of an individual. In other embodiments, a combination of two or more detection units may be used. For example, EMG detectors may be attached to an agonist and antagonist muscle group or signals from other combinations of muscles may be collected. In general, the EMG data collected in step 38 may be from any of various suitable types of electrodes, such as, for example, surface monopolar electrodes, bipolar differential electrodes or electrodes of another suitable geometry. Such electrodes may, for example, by positioned on the surface of the skin, may or may not include application of a gel, and may, in some embodiments, be Ag/AgCl electrodes. The use of a bipolar EMG electrode arrangement, e.g., with a reference lead and two surface inputs, allows for the suppression of noise that is common to those inputs. For example, a differential amplifier may be used, and a subtraction of the signals from one input with respect to the other may be executed. Differences in input signals, such as originating from depolarization of a muscle group, may therefore be selectively amplified and signals that are common to both inputs (such as external noise) may be substantially nullified. As previously noted, in some embodiments, calibration or normalization of electrodes may be periodically executed. Electrode normalization may, in some embodiments, include application of a test pulse, typically an alternating current, to either or both of the detection or reference inputs of an EMG detection unit. The output signal from the test pulse may be used to execute a calibration routine (such as involving adjustment of amplifier and/or digital signal gain settings).

In a step 40, the EMG signals may be processed by filtering to select a plurality of frequency bands of various widths. Filtering may be achieved using software or electronic circuit components, such as bandpass filters (e.g., Baxter-King filters), suitably weighted. Step 38 (collection of data) and step 40 (selection of frequency regions of interest) may be described conveniently as distinct steps. However, such description should not be interpreted as limiting methods herein to filtering with either software or electronic circuit components, for example, analog or digital signal processing—either techniques and or combinations of analog and digital signal processing may be used for isolation of spectral data. In some embodiments, three frequency bands may be selected including a first range, a second range, and a third range. The first range may range from about 250 Hz to about 420 Hz, or about 300 Hz to about 400 Hz, or about 325 Hz to about 375 Hz. The second range may range from about 80 Hz to about 290 Hz, or about 130 Hz to about 240 Hz, or about 150 Hz to about 220 Hz. The third range may range from about 10 Hz to about 50 Hz, or about 30 Hz to about 40 Hz, or about 32 Hz to about 38 Hz. In some embodiments, the frequency bands selected in a step 40 may be based on a measured waveform previously analyzed during a reference period. For example, during a reference period, spectral data from a seizure period may be measured and that data may be compared to or fit to a generalized GTC waveform. A GTC waveform includes a number of characteristic reference points which may be correlated to spectral data for a given patient. For example, a GTC waveform may show a region of depressed spectral density (local minimum) near about 280 Hz to about 320 Hz, a region of elevated spectral density (local maximum) near about 380 Hz to about 420 Hz, and an inflection point between local extreme values. Such characteristic reference points may be identifiable in different individuals but for those patients the points may be found at different frequencies. The position of those reference points may be associated with a patient's individual musculature, and for some individuals may be related to motor manifestations during a seizure. In some embodiments, the position of a characteristic reference point, including, for example, a local minimum value, a local maximum value, or an inflection point, may be used to select or adjust the position of at least one of a plurality of the plurality of selected bands used in a T-squared calculation. In some embodiments, the number of frequency regions selected for analysis may be greater than three. For example, some methods, particularly but not limited to those that use PCA analytical methods may involve the selection of greater than three ranges. Selection of frequency bands may be made by collecting EMG data for a period of time and converting the data using Fast-Fourier Transform (FFT) techniques. In some embodiments, data may be collected for an epoch of about one half second to about two seconds (or for some other period) and converted to the frequency domain.

In a step 42, EMG data (from the selected frequency regions) may be processed using any of various statistical techniques. For example, in some embodiments, data from three selected frequency ranges may be used to determine Hotelling's T-squared statistics. Hotelling's T-squared test assumes that data are independent and multivariate Gaussian. Those assumptions are generally invalid for EMG data; however, it has been discovered that Hotelling's T-squared statistic may serve as a metric for recognizing when amplitudes of measured powers in the selected frequency ranges have changed, thus possibly signaling a seizure episode. Accordingly, Hotelling's T-squared statistic may be considered a metric in which the amplitude of measured power for each frequency range is normalized by its variance and its covariance with the power amplitudes measured in other frequency ranges. This approach may produce a more sensitive and stable indicator of a seizure event or alarm condition than using the power in a single frequency range or using the total power for a combination of frequency ranges without convolution of the data by normalization of the data by its variance/covariance with other selected ranges. Importantly, because the system is more sensitive to seizure activity than, e.g., measurement of integrated power content over one or more frequency ranges, threshold values for detection may be increased (thus avoiding many false-positive detections) without missing the detection of a seizure. In some embodiments, a T-squared analysis may be executed upon the power amplitude within selected bands. In other embodiments, T-squared analysis may use other characteristics of the EMG data—alternatively, or in combination with power amplitudes. For example, the spectral density at one or more discrete frequencies in a given band, e.g., the peak spectral density in a certain band, or the mean spectral density within a band may also be processed with Hotelling's T-squared statistics. In addition, data from other sensors that may be present, such as, for example, temperature, accelerometer, or ECG data, may also be processed.

The T-squared calculation of step 42 may be based upon calculating the variances/covariances across the selected frequency ranges. The T-squared statistic can be calculated at each time point, e.g., generating 1024 statistics or 2048 statistics (depending upon the sampling rate) for each second of EMG data. Of course, other suitable sample rates may also be used as appropriate, for example, to avoid aliasing. Using three frequency ranges may result in a 3 by 3 positive symmetric variance/covariance matrix that may be inverted using a Singular Value Decomposition ("SVD") calculation. The variance/covariance matrix may thus be decomposed into its eigenvalues and orthonormal eigenvectors. The eigenvalues and eigenvectors may be used to calculate the inverse of the variance/covariance matrix and used for the T-squared calculations, such as by calculating weighting coefficients. The T-squared statistic may, for example, be used to combine the power amplitude of the three frequency ranges into a single T-squared statistical value.

In some embodiments, the T-squared calculation of step 42 may assign different weights to the signals from the selected frequency bands. The weighting factors applied in the step 42 may, for example, have been determined by analyzing the selected frequency bands during a reference-training period. The weight assigned to each of the frequency bands may, for example, be calculated from the inverse of the variance/covariance matrix of the selected frequency bands, such as may be calculated during the reference-training period. The weights assigned to each of the frequency bands may therefore be dynamically adjusted, either automatically such as during periodic normalization (and re-training) or, in some embodiments, by an operator. In this approach, a frequency range exhibiting more muscle activity (usually a lower frequency range) may be assigned less weight than a frequency range exhibiting lesser muscle activity (usually a higher frequency range). Appropriate weighting may depend upon an individual's normal muscle movement observed during a reference-training period and the particular frequency bands selected. For example, three bands may be selected as follows: Range 1 may range from about 300 Hz to about 400 Hz, Range 2 may range from about 130 Hz to about 240 Hz, and Range 3 may range from about 30 Hz to about 40 Hz. When using those bands, the weighting factors may be about 5% to about 20%, or about 8% to about 15% for Range 3, about 20% to about 40%, or about 25% to about 35% for Range 2, and about 50% to about 70%, or about 55% to about 65% for Range 1.

The T-squared statistic may be recalculated with any given interval of data collection, e.g., sampling frequency for an electrode, and it may be desirable to smooth the calculated value, such as using exponential smoothing, and compare the smoothed statistical value with reference data. Any of various suitable smoothing techniques (e.g., moving average filter, Savitzky-Golay filter, Gaussian filter, Kaiser Window, various wavelet transforms, and the like) may also be used. Generally, a smoothing factor alpha ($\alpha$) may range from 0 to 1, i.e., $0<\alpha\le1$. In some embodiments, a smoothing factor of 0.5 may be used. Generally, $\alpha>0.5$ may reduce the smoothing, and $\alpha<0.5$ may increase the smoothing. Increased smoothing may result in identification of fewer seizure events, thus potentially making the seizure alarms less responsive. A T-squared statistical value may be calculated at each interval of time in data collection and compared to a reference value (see step 46 below). The value compared to any given reference value may be a smoothed value and/or may be an average value from a certain time interval. For example, data collected over a period of about 10 milliseconds (which may include multiple T-squared calculations), may be averaged together and the average T-squared value compared to a reference T-squared value. Therefore, the number of comparison calculations between a T-squared value and a reference T-squared value (see step 46) may be the same or different from the number of times the T-squared statistic is calculated.

In some embodiments, a T-squared value may be an average value from a plurality of T-squared calculations or a discrete T-squared value. By collection of a plurality of T-squared values a standard deviation during a monitoring period (and/or another metric related to the variability of a data set) may be calculated. Such should not be confused with the standard deviation of a T-squared reference or baseline level (and scaling a T-squared calculation in units of standard deviations of a baseline or reference level—such as by evaluating a Z-factor). The standard deviation of a plurality of discrete T-squared calculations may, in some embodiments, be used as a metric in the determination of whether to initiate an alarm. Thus, in some embodiments, a T-squared value (such as a discrete value, average T-squared value or smoothed value), an alarm lag, a standard deviation of a plurality of T-squared values from a monitoring period, or any combination thereof, may be used to assess whether a seizure may be occurring.

Referring back to FIG. 4, in a step 44, the reference data (for subsequent comparison in step 46 with statistical value or values determined in step 42) may be determined or selected for use. The reference data may, in some embodiments, be selected from memory, such as by accessing a template file that may include a predetermined reference value. For example, a reference T-squared statistical value may be established from EMG data obtained during either a reference-training period, such as, for example, may have been conducted in a supervised setting, or may be selected for an individual of a certain patient demographic. In some embodiments, the reference value may be selected once (such as at the beginning of a monitoring period) and may simply be used in the many different calculations during continuous monitoring. However, in some embodiments, the reference T-squared value may be determined (and not simply selected) during a given monitoring period. For example, the apparatus may automatically self-train for a patient by calculating the variance/covariance matrix for the reference T-squared statistic using EMG data obtained when an individual is initially connected. For example, EMG data from a 10 minute period, such as minutes 2-12, may be used for training Other suitable time periods may also be used, such as, e.g., one minute, two minutes or five minutes. Such re-training may help the system in dealing with amplitude variation between periods of use. For example, the amplitude may vary between uses depending upon, e.g., placement of the EMG sensors. The apparatus may be normalized from session to session to account for, e.g., how tightly the EMG sensors are placed over a muscle, humidity, EMG sensor location, etc. In some embodiments, the system may delay for some lag period, e.g., two minutes or some other period, after connection of the electrodes before training. An individual may, e.g., tend to move their arms in a disproportionate manner after placement of a detection unit on the skin and the impedance of the skin may tend to stabilize over some period following attachment. During a training period (or re-training) an individual may be substantially at rest. In some embodiments, an individual may participate in most common daily activities during training, with the exception that strenuous activities may be avoided. While executing training, a detection system may also be monitoring for seizure activity. For example, during any given training (or re-training) period, the system may default to a stored setting, e.g., the system may default to a setting stored in a template file or to the last accepted value that had been used. If a seizure episode occurs during the training time, the seizure may be detected and the training could be moved to another interval.

In some embodiments, normalization of the system may occur periodically, such as, e.g., at regular intervals. Normalization of the system may alternatively or also occur when a sufficient increase or decrease in the average amplitude of the signal occurs and there has been no alarm in a previous time period, e.g., the preceding hour. In some embodiments, re-normalization may be performed at any time where the average amplitude changes by more than some rate. For example, a maximum acceptable drift in the amplitude of EMG signal may be denoted in a template file (e.g. Max. Amplitude Drift between calibrations).

In some embodiments, re-normalization may be performed at any time that false alarms are deemed to occur too often. For example, in some embodiments, an individual may be alerted that an alarm is being sent or is about to be sent. An individual, if alert and aware that they are in fact not experiencing a seizure, may be given the option of sending a message to a caregiver and/or to a data storage unit that a false positive was alerted by the system. In some embodiments, repetitive signaling that a false positive has been made may serve to initiate system re-calibration. In some embodiments, re-calibration may also be controlled manually, such as by the individual who is being monitoring or by a caregiver, e.g., an individual who may be remotely monitoring a patient. Following completion of re-normalization, reference values determined therein may be used in any subsequent comparison with statistical values determined from the EMG data.

In a step 46, one or more statistical values of the processed EMG data, such as, for example, a T-squared statistical value based on power amplitudes in different ranges (see step 42), may be compared to a reference value. The difference in T-squared statistical values ($\Delta$ T-squared) may, for example, be calculated as:

$$\Delta T\text{-squared} = (T\text{-squared statistic}) - (\text{ref. } T\text{-squared}) \quad \text{(Equation 1)}$$

where:
$\Delta$ T-squared=Difference between a T-squared statistical values calculated during a monitoring period and a reference T-squared value
T-squared statistic=Hotelling's T-squared statistical value determined from data obtained in a monitoring period
Ref T-squared=Hotelling's T-squared statistical value determined from data obtained in a reference-training period or from data of a certain patient population As previously described, in some embodiments, the reference T-squared value may be adjusted, such as during periodic normalization (such as by detector normalization and system training or re-training) to be a value that is low. Thus, in some embodiments, a reference T-squared value may be included in the calculation of $\Delta$ T-squared and, in some embodiments, may be assumed to be zero.

In a step 48, the determined statistical values and/or the comparison of those values with reference values may be used to determine the likelihood that a seizure event may be occurring. In some embodiments, a Z-value, e.g., units of standard deviation in which statistical factors (T-squared values) differ, may be determined. For example, the Z-value may be calculated as follows:

$$Z\text{-value} = [\Delta T\text{-squared}] / [(\sigma) \text{ref. } T\text{-squared}] \quad \text{(Equation 2)}$$

where:
Z-value=Difference between T-squared statistical values scaled in units of standard deviations
$\Delta$ T-squared=Difference between T-squared statistical values calculated from data obtained during the monitoring period and calculated from data obtained in a reference training period
($\sigma$) ref. T-squared=standard deviation of the T-squared baseline The Z-value may therefore scale the value of $\Delta$ T-squared in units of standard deviations from a T-squared baseline determined during a reference period. The standard deviation of a T-squared baseline used for scaling Z-factors may be determined from a reference period (or a reference period consecutive with) that is also used as a reference-training period used for calculation of weighting coefficients. In other embodiments, the reference periods may not be concurrent with a reference-training period used for determination of weighting coefficients. For example, a reference period where a patient is undergoing certain activities may be used to determine a standard deviation and may be executed in a supervised setting, and a reference period for establishing weighting factors may be executed during daily home use. In some embodiments, a threshold T-squared value may be also be used and comparison of a T-squared value may be made to a threshold T-squared value (such as determined using an MVC or determined based on one or more demographic criteria).

If the Z-value is found to exceed a threshold Z-factor, a decision to initiate an alarm protocol may be made. For example, an assessment of whether to initiate an alarm may be:

If Z-Value>threshold Z-factor (initiate alarm protocol)  (Equation 3)

If Z-Value<threshold Z-factor (do not initiate an alarm)  (Equation 4)

In some embodiments, the sensitivity of the alarm to the magnitude of the T-squared statistics could be adjusted. The threshold Z-factor used to trigger an alarm condition may be set to a higher value. A higher threshold Z-factor may serve to reduce the frequency of false alarms. A threshold Z-factor may, for example, be one standard deviation from the baseline T-squared value. Thus, a Z value of 1 is one standard deviation from the T-squared baseline determined during the training period, a Z value of 2 is two standard deviations from that baseline, a Z value of 3 is three standard deviations from that baseline, and so forth. Increased muscle activity (higher amplitude EMG signals) resulting from a seizure may produce a larger T-squared value, and a user may, for example, set a threshold Z-value at 3 to ensure that muscle activity must reach a certain amplitude level before an alarm condition is reached. Generally, lower values of threshold Z-values may create more false alarms, and higher threshold Z-values may be used to reduce the frequency of false alarms.

The selection of a suitable threshold Z-factor may depend upon the settings used. For example, weighting factors for the selected frequency bands may influence the response of the system to motor manifestations, noise sources, and seizures. In addition, system training and calculation of the variance/covariance matrix for calculation of the T-squared values may influence the magnitude of the threshold Z-factor. For example, if a weighting factor for a low frequency band is high, the system may be more responsive to some motor manifestations (such as with typical muscle activity). In addition, for such weighing factors the T-squared statistic may not change as rapidly when higher frequency signals are sent to maintain the muscle contraction. Decreasing the weight associated with the low frequency band may increase the system sensitivity to high frequency motor manifestations. However, low frequency weighting factors that are too low may result in attenuation of overall signal strength.

Use of frequency bands and relative weighting factors as described herein may produce T-squared statistics that yield highly stable baselines (even when an individual is performing some common daily activities). Importantly, such may provide T-squared values that increase rapidly and selectively to the types of muscle activity that may be present when a seizure occurs and thus high threshold Z-factors may be used. Such may be advantageous because false positive detections may be greatly reduced, even for individuals who are mobile and/or individuals who may engage in rigorous daily activities. In some embodiments, threshold Z-factors may be as high as about 1000 yet may still capture seizure activity. Accordingly, threshold Z-factors herein may, in some embodiments, be up to about 1000 or even higher, or may be about 45 to about 1000.

In some embodiments, an MVC calculation may be used to set the threshold Z-factor. For example, the threshold Z-factor may be set such that a T-squared value, in order to exceed the threshold Z-factor, is some factor (N) of the difference between T-squared statistical values calculated during MVC (reference T-squared MVC) and while the individual is at rest. For example, to set the threshold Z-factor to a factor (N) between T-squared statistical values, the threshold Z-factor may be calculated as:

threshold Z-factor=$N[((\text{ref. }T\text{-squared-MVC})-(\text{ref. }T\text{-squared}))/(\sigma)\text{ref. }T\text{-squared}]$ The value of a threshold Z-factor, alarm lag or combinations thereof may be used in assessment of whether a seizure event may be occurring. If the system deems that a seizure may be occurring, the system may initiate an alarm protocol (step 50). Of course, in determining whether an alarm is initiated, the system may store in memory and analyze any number of Z-values. For example, if the alarm lag is set to be 2 seconds, Z-factors from a suitable number of preceding measurements may be considered. Alternatively, the system may deem that a seizure is not present and, for example, collect a next cycle of EMG data and repeat assessment of whether a seizure may be occurring.

As shown in FIG. 4, steps 46 and 48 describe comparison of processed EMG data to reference data (or valued derived from that data) and using that data to determine if a seizure may likely be occurring. As previously noted, reference data may be selected from a template file, and a patient may not need to re-train the detection unit every day. Rather, a user may attach the detection unit, and established reference data may be downloaded and used to analyze EMG derived statistical values. A template file, may, for example, include various constants used in either of steps 46 and 48 to treat or analyze collected data. Some of the information that may be included in such a template file is shown in Table 1. For clarity, the "XX" is simply a placeholder, and should not be construed to connote magnitude or precision in any way.

TABLE 1

List of some constants that may be found in a template file

| Variable | Value/unit | Type |
| --- | --- | --- |
| Threshold Z-value | XX (standard deviations) | Criterion for analysis of alarm state |
| Alarm lag setting | XX (seconds) | Criterion for analysis of alarm state |
| Smoothing factor ($\alpha$) | XX | Data processing factor |
| Bandpass filter width | XX (seconds) | Selection routine |
| Reference T-squared Default Value | XX | Data processing factor |
| Standard Deviation of the T-squared reference | XX | Data processing factor |
| Max. Amplitude Drift between calibration | XX (mV) | Selection routine |
| Max. Amplitude Drift Rate between calibration | XX (mV/sec) | Selection routine |
| Frequency range for band 1 | XX (Hz) | Selection routine |
| Frequency range for band 2 | XX (Hz) | Selection routine |
| Frequency range for band 3 | XX (Hz) | Selection routine |
| Frequency range for band N | XX (Hz) | Selection routine |
| Weighting factor Region 1 | XX | Data processing factor |
| Weighting factor Region 2 | XX | Data processing factor |
| Weighting factor Region 3 | XX | Data processing factor |
| Weighting factor Region N | XX | Data processing factor |
| Algorithm Type | XX | Selection routine |
| Filter window length | XX (seconds) | Selection routine |

It is envisioned, at least in some circumstances, that at least some of the initially selected values for a template file may be established by grouping an individual into a patient demographic. For example, in some embodiments, an initial template file may be obtained using historical data from a general patient demographic. A patient may, for example, be defined by various characteristics including, for example, any combination of age, gender, ethnicity, weight, level of body fat, fat content in the arms, fat content in the legs, mid upper arm circumference, fitness level, level of one or more maximum voluntary contractions, or the patient may be defined by other characteristics. The patient's medical history including, for example, history of having seizures, current medications, or other factors, may also be considered. To establish settings for a given patient based on the particular patient demographic to which that patient matches archived data for other patients in that particular demographic may be used. The archived data may include EMG data together with an indication of whether or not the data is associated with a non-seizure or seizure period. As data is collected for a given patient, that data may be added to the data library. Once a template file is generated or selected, it may be included in computer memory within a detection unit, base unit, or both, and an individual may use the detection unit in a home-setting.

Settings for the device may also be established from patient monitoring during a training period, e.g., the patient may be monitored in a supervised setting. For example, during monitoring data may be collected for determining general seizure characteristics. The patient may, for example, be monitored with EMG over a period of several days, or some other interval, as necessary to collect data associated with a statistically significant number of seizures. During the period of monitoring, patient EMG data may be collected. EMG data from time periods with known seizures and also intervals with non-seizure periods may be collected, archived, and an operator may analyze the data and determine a reference value for use. An operator may, for example, analyze the data and may import various different hypothetical values into a template file. The system may then, using the hypothetical values, simulate, e.g., whether any alarms or false positives would have been issued based on the recorded data. The operator may select values for a template file based on the data or based on values typical for all patients or for patients of a certain demographic.

In some embodiments, a reference training period may also involve measurement of the Maximum Voluntary Contraction (MVC) of a patient or measurement of the electromyographic signatures thereof. For example, a patient may execute a voluntary contraction under conditions of maximum effort and the electromyographic signal recorded. As the strength of muscle varies from individual to individual, the amplitude of EMG signals may vary as well; therefore, having the patient perform the MVC may tailor device settings to that individual's musculature. The MVC may be used to assist the operator in setting sensitivity values, such as threshold Z-value and/or alarm lag, for a patient. The MVC may be particularly useful for patients who experience seizures only infrequently and for whom it may be difficult to gather seizure-significant-statistical data for seizures during a reasonable training period.

In some embodiments, an apparatus and method of detecting seizures using EMG signals could include a number of steps. For example, in some embodiments, the detection unit and/or base station may be placed in a "sleep" mode until signal activity warrants continuous monitoring. When in "sleep" mode, the base station may periodically poll the detection device for leads-off detection and signal monitoring. Such embodiments may be used to organize the collection of portions of data that are most relevant, e.g., portions of data most likely to include a seizure.

Figure 5:
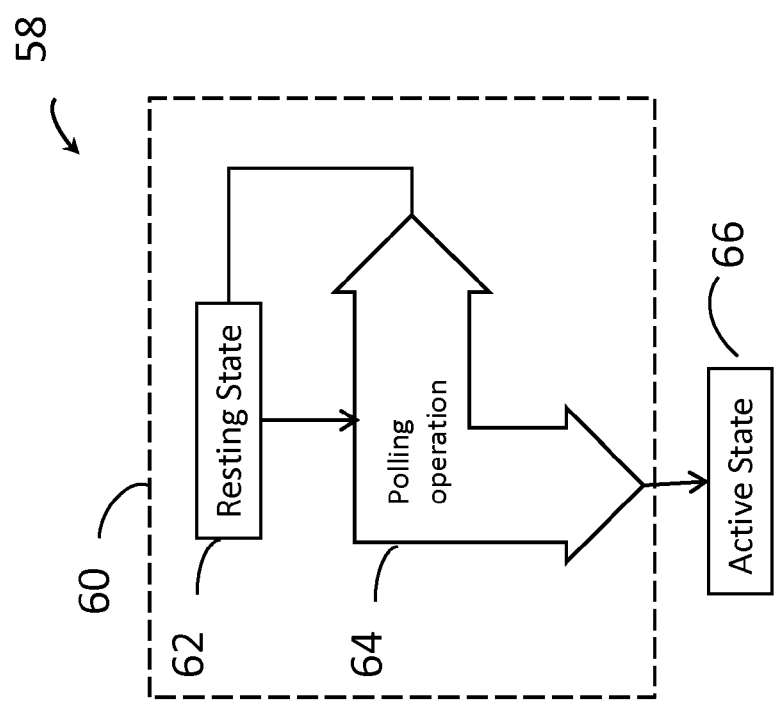
FIG. 5 illustrates one embodiment of a method of adjusting the state of a detection unit in a method of seizure monitoring.

For example, FIG. 5 illustrates one embodiment of a method 58 of detecting seizures. In method 58, the rate of data collection depends upon the state of the detection unit. Method 58 may, for example, be used to toggle a detection unit and/or base station between a "sleep" mode, i.e., characterized by operations within dashed line 60, and a mode of substantially continuous operation, such as active state 66. As shown in FIG. 5, a detector and/or base unit may be configured to exist in the resting state 62 for a portion of time while in a "sleep mode." While in the resting state 62, a detector or base unit may be silent, e.g., it may not be monitoring or collecting data from a patient. The resting state may include instructions to periodically exit the resting state 62 and, for example, collect detector data for a period of time. That is, a detector may enter a polling operation step 64 where data is collected. The duration of an individual polling operation may be sufficient to collect data as needed to make a decision regarding the state of the detection unit. That is, for example, based on data collected during polling step 64, a detection unit may revert back to the resting state 62 or may enter another state, such as active state 66. Once placed in active state 66, the detection unit may, for example, monitor electrical activity in a continuous or substantially continuous manner.

For example, if threshold Z-value and alarm lag thresholds are exceeded, then an alarm may be sent, e.g., to the base station together with data. The base station may separately process the data for verification of the alarm condition. If the base station agrees with the alarm, then the base station may generate an alarm to remote devices and local sound generators. An alarm or alert may comprise an audible signal, or pre-recorded voice message, or a text message, or email, or trigger vibration in a PDA, or other suitable attention-getting mechanisms. The patient's detection unit or base station may further comprise GPS technology, such as that used in smartphones and handheld navigation devices, to allow a caregiver to determine the patient's location. An alarm or alert may comprise patient location information.

In other embodiments, a unitary device may be used without the need for a base station or other remote data processing capabilities. The unitary device may process the EMG data and send an alarm to a caregiver when the threshold Z-value and alarm lag thresholds are exceeded. A unitary device may comprise a small, battery-powered mobile device attachable over a patient's muscle that may communicate an alarm to a caregiver via network communication, such as cellular telephony. The unitary device may further comprise GPS technology to allow a caregiver to determine the patient's location. Again, the alarm or alert may comprise patient location information.

In some embodiments, a detection unit may (if appropriately triggered) send an alarm to a base station (such as by 802.11 protocols) and also send communication from the patient worn detection unit to a remote cell phone or other hand-held device via Bluetooth™. The communication may also, e.g., direct the cell phone to dial out to a predetermined phone number, e.g., by sending a txt message, and if a person answers on the other end answers, to open a voice-comm link. Thus, various functions that may be executed by a base station may also be executed by a cell phone. One advantage of having both a base station and cell phone contacted, i.e., via Bluetooth™, is that the two transmission means may have different working distances. Thus, a patient may be free to move between locations without risk of losing a monitoring connection.

In some embodiments, having the base station (or smart phone with a suitable installed application) agree to the detection unit's alarm introduces a voting feature. With such a feature, both devices must vote on the decision and agree to trigger the alarm. This process may limit false alarms. In such embodiments, the detection unit may process the signal data, and send both the results and the raw data to a base station. The base station may independently process the signal data and compare its results to the results sent by the detection unit. As noted above, the base station may have greater processing power, and thus, be able to process more time periods than the detection unit and to do so with more advanced algorithms. If the base station results confirm a detection of seizure-related activity made by the detection unit, then an alarm may be generated, e.g., a message sent to a caregiver. If the base station results differ from those of the detection unit, the detection unit's results may be flagged as a false positive. Initially, the detection unit results may be given a weight that is more likely to trigger an alarm (even if contradicted by the base station), and if false positives are generated, the method may adapt to the patient to reduce false positives, such as by adjustment of seizure detection threshold settings including Z-factor settings, lag settings or weighting coefficient settings.

In some embodiments, a detection unit may use an algorithm that calculates a T-squared statistical value. Comparison of the T-squared statistical value to a reference T-squared statistical value (and determining a Z-factor, e.g., the number of standard deviations by which the T-statistical value differ) may be used to monitor the patient's state. The algorithm may further use lag settings as needed to adjust the system sensitivity. To simplify the detection unit calculation, a limited number of frequency regions may be selected and a limited number of weighting factors may be used in the detector unit calculation. The base station, which again, may have greater processing power, may, in some embodiments, apply a number of different algorithms including, e.g., variations of frequency regions, weighting factors and other criteria, to evaluate whether a seizure may be occurring. The base station may also apply an algorithm that, e.g., uses a T-squared statistical value to log an event in a register. Additional registers may be associated with other data characteristics, such as, e.g., the presence of a characteristic GTC waveform, the presence of data bursts, or to other characteristics, such as described in U.S. application Ser. No. 13/275,309. Analysis of events logged in registers for different characteristics of the output data may be used to assess whether a seizure incident is declared and whether an alarm is sent to one or more locations.

During or after a seizure event, a human operator may review and adjust the threshold Z-factor and alarm lag settings based upon the severity of the seizure or possibly the non-detection of an actual seizure because of too-sensitive settings. Many people have seizures and do not realize that they had a seizure, e.g., the short-lived seizures discussed above. Having stored data to review may help medically manage the person with seizures. Also, a human operator may evaluate the data and, based on activities known to have occurred during the time of monitoring, conclude that a seizure did not occur, and either cancel the alarm or instruct the monitoring system that the detected waveform did not indicate a seizure. Likewise, a human operator may instruct the monitoring system that an undetected seizure had occurred by, e.g., specifying the time during which the seizure occurred. For example, an operator may be provided with EMG data which comprise a rolling "window" of EMG activity, and the human operator may "rewind" the recorded signal and indicate to the monitoring system the time window in which the seizure occurred. In some embodiments, the base station may visually depict the signal and provide a graphic user interface (GUI) that allows human operators to accomplish the "window" selection and define other operating thresholds and conditions. The monitoring system may thus have additional data points against which to evaluate future seizure events for that particular patient.

An apparatus for detecting seizures may be man-portable, and may include a detection unit that may be attached to the body, such as by use of an elastic arm band. The detection unit may be battery powered, and may wirelessly communicate with the base station. The detection unit may include sufficient data storage, processing and transmission capability to receive, buffer, process and transmit signals. The detection unit may process the signals and conduct a simplified analysis, e.g., using fewer T-squared calculations or PCA components. When the detection unit determines that a seizure is occurring, it may download both its analysis and the raw signal data to a bedside base station for more complex processing. The base station may have much more power, larger storage capability and greater processing speed and power, and be better equipped overall to process the information. It could, for example, perform more T-squared calculations. Likewise, the base station may transmit raw and processed signal data to a remote computer for further analysis and aggregation with signal data from other units in use. For example, multiple base stations may transmit data for multiple patients to a remote computer. Each base station may not receive the other base station's data, but the remote computer may serve as a common repository for data. Aggregation of the data may allow further data points from which to further refine the baseline thresholds, alarm sensitivity thresholds and statistical information that may be supplied to base stations and detection units as a factory default or upgrade.

Figure 6:
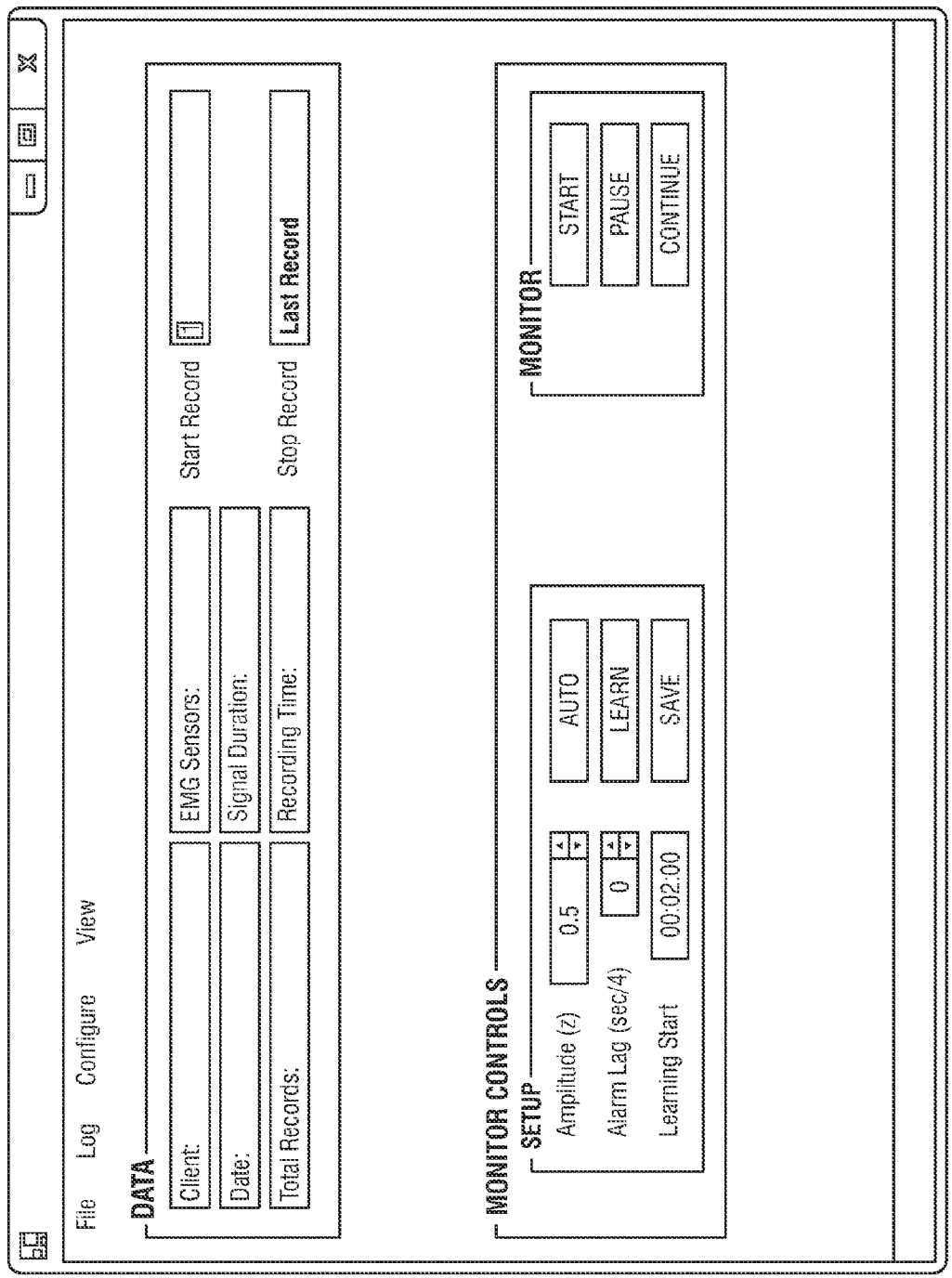
FIG. 6 illustrates a graphical interface that may be used for accessing data files.

The system described herein may, in some embodiments, be configured to allow a caregiver to monitor and/or adjust various system settings. For example, the system may be accessed by caregivers at the point of monitoring, and used, e.g., to modify system constants (e.g., adjust sensitivity), review the patient history, family history, current or past medications, compliance to a medication regimen, or create a log of seizure incidents to help medically or surgically manage the patient. Exemplary aspects of some embodiments of a system interface, are illustrated in the exemplary FIGS. 6, 7A-7D, 8, 9A-9D, 10A-10D and 11. For example, the base station may be programmed to provide a user interface to allow a caregiver to select various processing, analysis, alarm and other options. A base station may, for example, provide a caregiver with a graphical user interface similar to that of FIG. 6 which may allow a user to both record, process and analyze EMG data as it is collected in real-time, or process and analyze previously-recorded EMG data. As may be seen in the embodiment of FIG. 6, a user may be able to enter in the Client field the name or ID number of the patient to be monitored or whose records are to be reviewed. In the Date field, the user may enter the date of monitoring. In the EMG Sensor field, the user may select the number of EMG sensors that are to be used (such as 1 or 2 sensors). In addition, the user may adjust the system's sensitivity, such as, e.g., by setting the threshold Z-value and alarm lag settings, such as in quarter-second intervals or in some other interval. In some embodiments, the threshold Z-factor may range from 1 to 500 or more. In some embodiments, an adaptive algorithm may use feedback from the user regarding false alarms to automatically adjust the Z-factor and/or alarm lag to reduce sensitivity, e.g., by incrementing the values together or alternately.

In addition, in some embodiments, a user may be able to place the system in training mode. For example, the software may give the user an option to select the Learn button and the user may identify a time at which the learning period should start. In addition, the user may, e.g., automate the learning by selecting the "Auto" button or prompting the system to re-train in some other way. The user may save the settings by selecting the Save button. A user may start the monitoring and recording process by selecting the Start button, and pause and resume the monitoring and recording process by selecting the Pause and Continue buttons, respectively. In brief, the system may generally allow a user to manually adjust or select a given routine from within the system functionality.

Figures 7A, 7B, 7C:
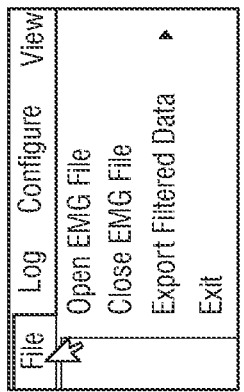
FIGS. 7A-D illustrate one embodiments of a user interface that may let a user to select and view EMG data.

In addition, the system described herein may include functionality to search for and/or download previous recordings. For example, if a user desires to process a previously recorded set of EMG signals, such as opening a previously-recorded file, or by looking at earlier portions of current monitoring sessions, a user may do so. A user may, for example, open or close a previously-recorded EMG file through a drop-down menu under File, similar to that illustrated in FIG. 7A. By default, the patient information fields in the Data box of the embodiment of FIG. 6 may be blank. If a user opens an EMG file, those fields may be automatically populated, as illustrated in FIG. 7B. As illustrated in FIG. 7B, an EMG file may be selected and opened, e.g., the EMG file selected in FIG. 7B is for recording 075950 of patient A begun on Jan. 2, 2011, at 10:36 pm (the EMG file of which is discussed in relation to FIG. 12). In this example, the complete file comprises approximately 8 hours of data and contains over 58 million records. A user may select, for example, only the first 8 million records for extraction if, for example, it is known that an episode on that day occurred only once starting approximately 50 minutes into the monitoring session, and lasted for approximately 15 minutes. Alternatively, a user may specify that the data should be processed all the way to the last record. In other embodiments, a user may specify a time range from which to process data, as may be seen in the embodiment of FIG. 8C.

Figure 7D:
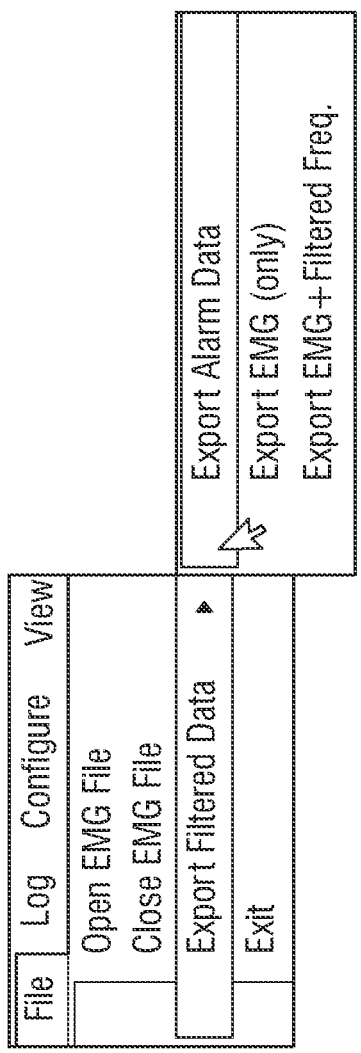
Figure 8:
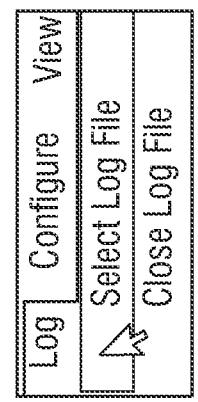
FIG. 8 illustrates one embodiments of a user interface associated with selecting a file.

A user may, in some embodiments, export an EMG file to another program for additional processing, as may be seen in the embodiment of FIG. 7D. For example, after reading an EMG file and running an alarm analysis, the data may be exported to a tab-delimited text file that can be imported into other software for analysis and graphing, such as STATA, SAS and JMP. Users may, for example, export alarm data comprising two columns: the T-squared value (or PCA value) for each record, and the alarm state. The alarm state may, for example, be depicted by a value of either zero or one. A value of one may indicate that the alarm was signaled at a certain time. The EMG value(s) may also be exported without prior processing.

In addition, the EMG values together with the extracted frequency bands can be exported. For example, if two channels, e.g., EMG27 and EMG28, are being used, data from those channels may be exported and each frequency band may have two values, for example, one for each of the two EMG sensors. A user interface may also allow a user to open and close log files, as may be seen in the embodiment of FIG. 8. The base station may automatically open and close a log file, log.txt, that can be viewed with a text processor. The Log portion of the main menu may allow a user to rename the log file and select where the log file should be stored. A user may also close that file and open another log file at any time. Log files may be used to debug problems that occur using the software.

A user interface may also provide a Configure menu, as may be seen in the embodiment of FIG. 9A. The Configure portion of the main menu may allow a user to test the effectiveness of alternate algorithms. By default, Hotelling's T-squared statistic may be selected. Alternatively, a PCA analysis may be conducted. The absolute values of the extracted frequencies may be processed instead of the actual value. The extracted frequency values may generally oscillate around zero with about half of the values being negative. By default these negative values may be used to calculate the T-squared and PCA statistics. However, by selecting "absolute values" all negative values may be replaced with their absolute, non-negative value.

For example, in the embodiment of FIG. 9B, three signal frequency bands may be selected for processing. By default, three frequency bands may be automatically selected: 300-400 Hz, 130-240 Hz and 30-40 Hz. Moreover, additional bands, such as, e.g., two additional bands may be selected for other frequency ranges.

Additionally, as may be seen in the embodiment of FIG. 9C, a user may select the width of the bandpass filter. By default, 0.25 seconds may be used for the width of the filter. If you select 0.25 seconds you may be selecting 0.25 seconds on either side of a given data point. More generally, the width of a filter may range from about 0.10 seconds to about 0.50 seconds. Therefore, the filter may use 1025 records for each filter calculation, corresponding to 0.50 seconds of data within a sample frequency of 2048/sec.

As may be seen in the embodiment of FIG. 9D, a user may select a particular patient recording. Selecting a patient recording may allow the system to use prior patient recordings to configure a system for another recording for that patient. These selections may automatically tailor the start and stop record numbers, and the sensitivity values to the best found for that recording or for that patient.

The user interface may also allow a user to view various data by interacting with the View menu. As may be seen in the embodiment of FIG. 10A, the Client Information menu item may provide a user with information related to a patient, such as the information shown in FIG. 7B. Additionally, episode information may be viewed, if any, as may be seen in the embodiment of FIG. 10C. If a record contains one or more seizure episodes, the start and stop records of those episodes may be displayed to the user. Alternatively, the start and stop times of those episodes may be displayed to the user.

Figure 10A:
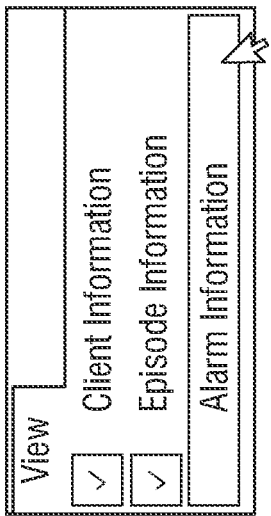
FIG. 10A-D illustrate one embodiment of a user interface that may let a user to view patient related information.
Figure 10B:
Figure 10D:
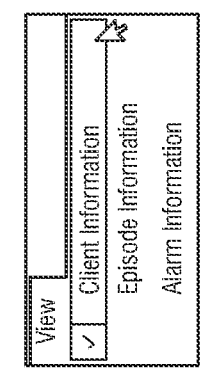
Figure 10C:
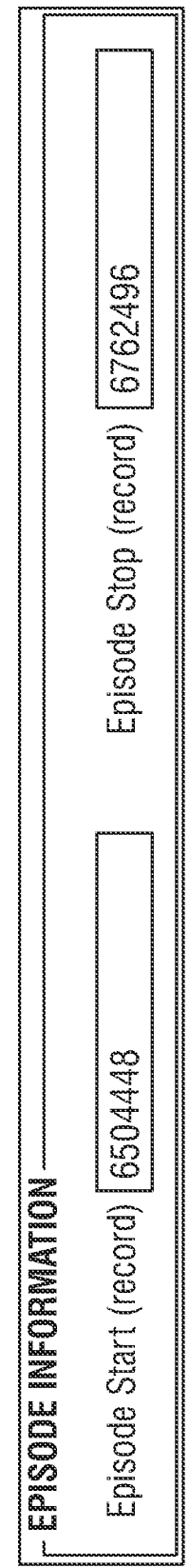

The View menu may also provide a user with a way to view alarm information, as may be seen in the embodiment of FIG. 10D. In some embodiments, a user may only select the Alarm Information menu item after running an alarm analysis. The alarm analysis may process the entire data with the signal processing configuration specified, e.g., with Hotelling's T-squared. The alarm analysis may display a popup window that summarizes the alarms found. If a user closes that window and later wants to view it again, the user may select View->Alarm Information.

Generally, the devices of a seizure detection system may be of any suitable type and configuration to accomplish one or more of the methods and goals disclosed herein. For example, a server may comprise one or more computers or programs that respond to commands or requests from one or more other computers or programs, or clients. The client devices, may comprise one or more computers or programs that issue commands or requests for service provided by one or more other computers or programs, or servers. The various devices in FIG. 1, e.g., 12, 13, 14, 16, 17, 18 and/or 19, may be servers or clients depending on their function and configuration. Servers and/or clients may variously be or reside on, for example, mainframe computers, desktop computers, PDAs, smartphones (such as Apple's iPhone™, Motorola's Atrix™ 4G, and Research In Motion's Blackberry™ devices), tablets, netbooks, portable computers, portable media players with network communication capabilities (such as Microsoft's Zune HD™ and Apple's Tod Touch™ devices), cameras with network communication capabilities, wearable computers, and the like.

A computer may be any device capable of accepting input, processing the input according to a program, and producing output. A computer may comprise, for example, a processor, memory and network connection capability. Computers may be of a variety of classes, such as supercomputers, mainframes, workstations, microcomputers, PDAs and smartphones, according to the computer's size, speed, cost and abilities. Computers may be stationary or portable, and may be programmed for a variety of functions, such as cellular telephony, media recordation and playback, data transfer, web browsing, data processing, data query, process automation, video conferencing, artificial intelligence, and much more.

A program may comprise any sequence of instructions, such as an algorithm, whether in a form that can be executed by a computer (object code), in a form that can be read by humans (source code), or otherwise. A program may comprise or call one or more data structures and variables. A program may be embodied in hardware or software, or a combination thereof. A program may be created using any suitable programming language, such as C, C++, Java, Perl, PHP, Ruby, SQL, and others. Computer software may comprise one or more programs and related data. Examples of computer software include system software (such as operating system software, device drivers and utilities), middleware (such as web servers, data access software and enterprise messaging software), application software (such as databases, video games and media players), firmware (such as device specific software installed on calculators, keyboards and mobile phones), and programming tools (such as debuggers, compilers and text editors).

Memory may comprise any computer-readable medium in which information can be temporarily or permanently stored and retrieved. Examples of memory include various types of RAM and ROM, such as SRAM, DRAM, Z-RAM, flash, optical disks, magnetic tape, punch cards, EEPROM. Memory may be virtualized, and may be provided in, or across one or more devices and/or geographic locations, such as RAID technology.

An I/O device may comprise any hardware that can be used to provide information to and/or receive information from a computer. Exemplary I/O devices include disk drives, keyboards, video display screens, mouse pointers, printers, card readers, scanners (such as barcode, fingerprint, iris, QR code, and other types of scanners), RFID devices, tape drives, touch screens, cameras, movement sensors, network cards, storage devices, microphones, audio speakers, styli and transducers, and associated interfaces and drivers.

A network may comprise a cellular network, the Internet, intranet, local area network (LAN), wide area network (WAN), Metropolitan Area Network (MAN), other types of area networks, cable television network, satellite network, telephone network, public networks, private networks, wired or wireless networks, virtual, switched, routed, fully connected, and any combination and subnetwork thereof. The network may use a variety of network devices, such as routers, bridges, switches, hubs, repeaters, converters, receivers, proxies, firewalls, translators and the like. Network connections may be wired or wireless, and may use multiplexers, network interface cards, modems, IDSN terminal adapters, line drivers, and the like. The network may comprise any suitable topology, such as point-to-point, bus, star, tree, mesh, ring and any combination or hybrid thereof.

Wireless technology may take many forms such as person-to-person wireless, person-to-stationary receiving device, person-to-a-remote alerting device using one or more of the available wireless technology such as ISM band devices, WiFi, Bluetooth, cell phone SMS, cellular (CDMA2000, WCDMA, etc.), WiMAX, WLAN, and the like.

Communication in and among computers, I/O devices and network devices may be accomplished using a variety of protocols. Protocols may include, for example, signaling, error detection and correction, data formatting and address mapping. For example, protocols may be provided according to the seven-layer Open Systems Interconnection model (OSI model), or the TCP/IP model.

Additional information related to the methods and apparatus herein described may be understood in connection with the examples provided below.

EXAMPLE 1

Figure 11:
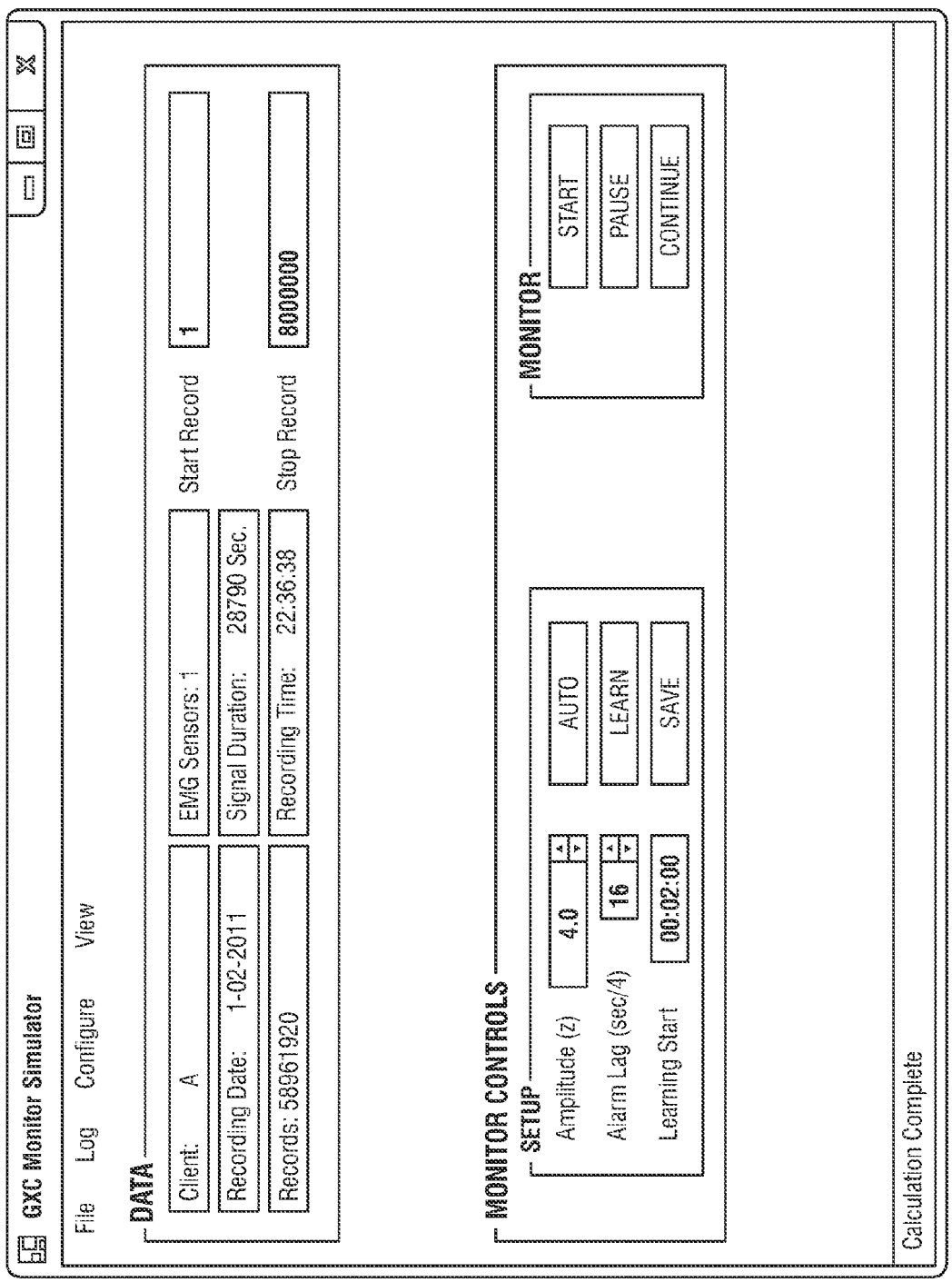
FIG. 11 illustrates one embodiment of a user interface that allows a user to access and review information associated with a patient.
Figure 12:
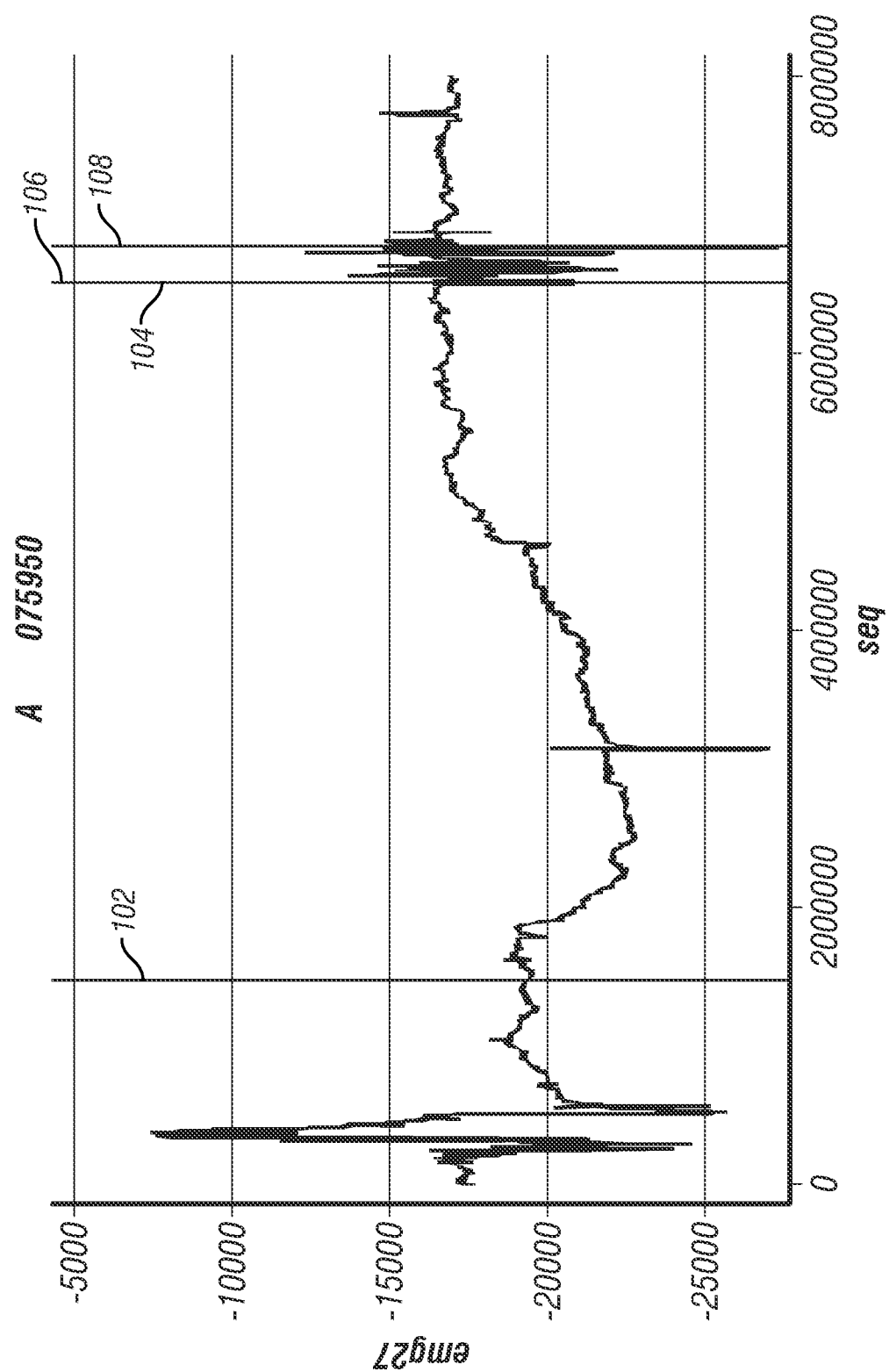
FIG. 12 illustrates one an EMG trace for a patient showing a monitoring period that includes a training region and an episode region.
Figure 13:
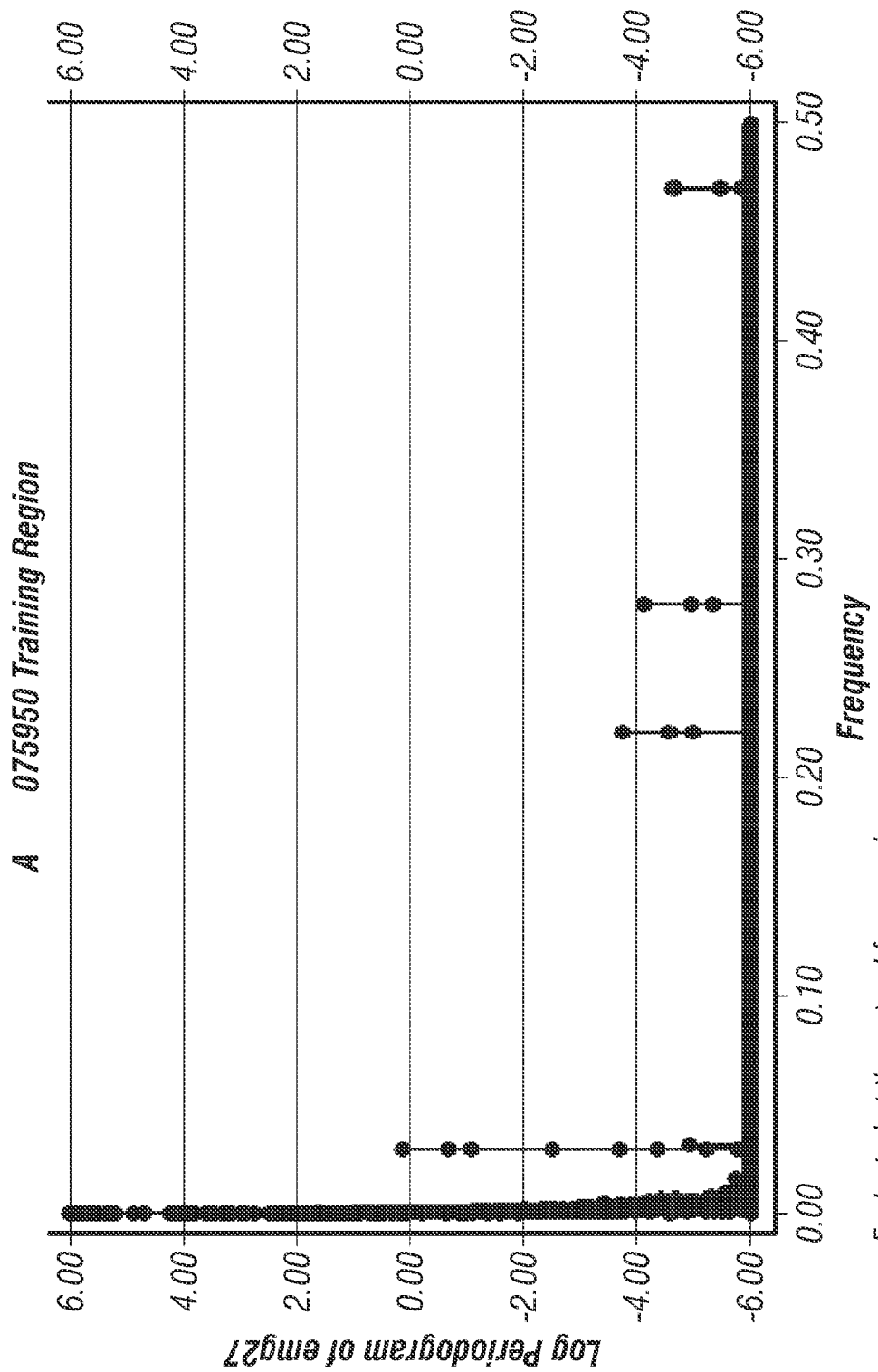
FIG. 13 illustrates a log periodogram of the training region for the EMG trace illustrated in FIG. 12.
Figure 14:
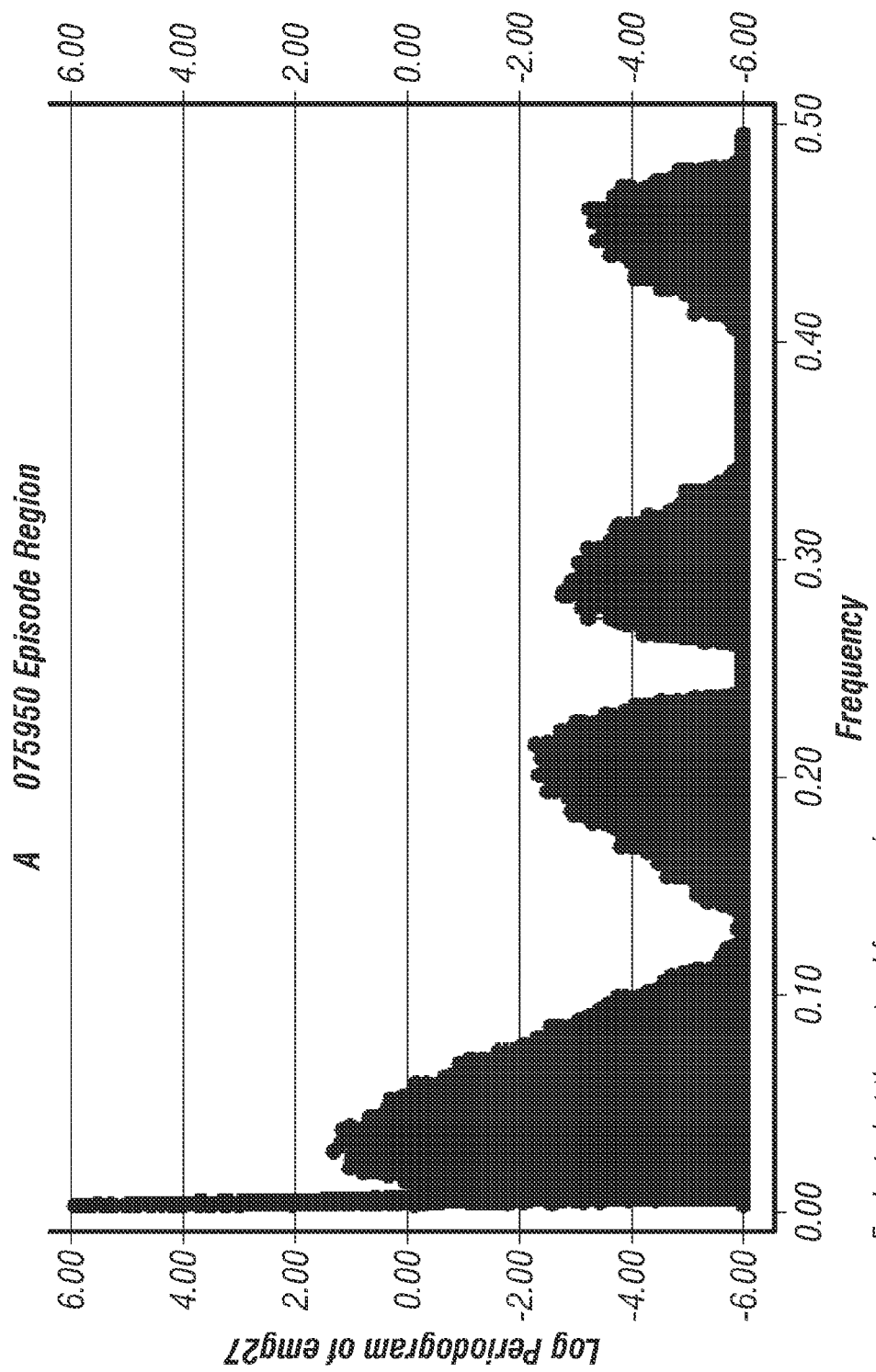
FIG. 14 illustrates a log periodogram of the episode region for the EMG trace illustrated in FIG. 12.
Figure 15:
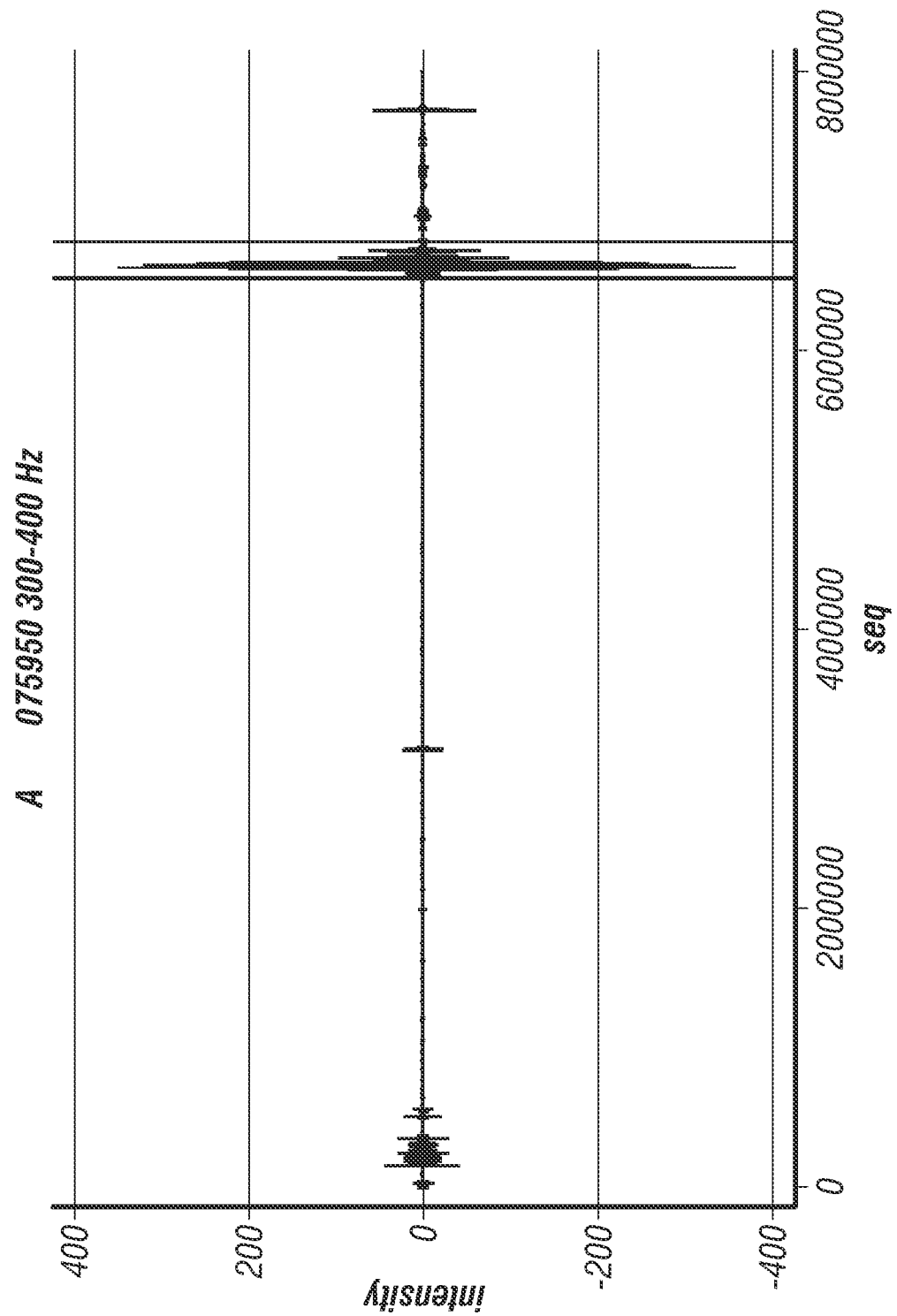
FIG. 15 illustrates the EMG waveform of FIG. 12 filtered to pass a frequency range of about 300-400 Hz.
Figure 16:
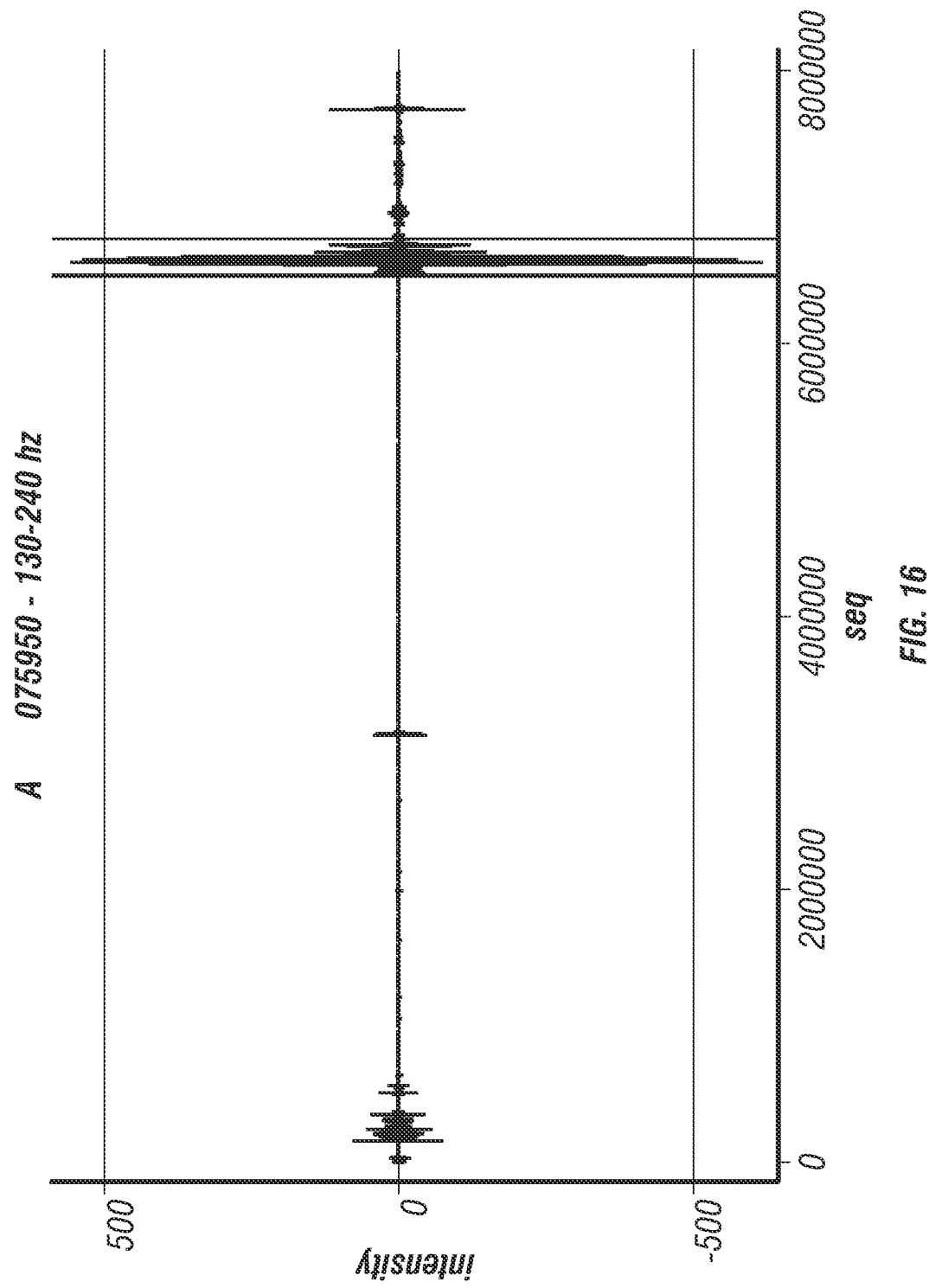
FIG. 16 illustrates the EMG waveform of FIG. 12 filtered to pass a frequency range of about 130-240 Hz.

In one example, data for an individual, i.e., patient A, was recorded. Data from that recording may be accessed remotely or may be accessed through a user interface configured on a base station. For example, as shown in FIG. 11, the base station software enables a user to access and review information. As shown in FIG. 11, the interface may allow a user to select the patient's records, e.g., first ~8 million from the EMG file 075950, for display. The records may be selected and displayed, as shown in FIG. 12. In this particular example, electrodes were connected to a patient during a period where the patient was particularly prone to experiencing a seizure. For the recording illustrated in FIG. 12, a 10-minute training period was started 2 minutes into the monitoring session. In FIG. 12, a first vertical line 102 to the right of the Y-axis has been drawn at approximately 12 minutes to denote the end of a training period. FIG. 13 shows the log periodogram of the training region. As indicated therein, and as evident by comparison of FIG. 13 to FIG. 14 (which shows the log periodogram of an episode region), only relatively low amplitude signals are present across a majority of the spectrum.

Referring back to FIG. 12, the period between vertical line 102 and vertical line 104 denotes a period where EMG data was collected without initiation of an alarm. For illustration purposes, the next three vertical lines roughly mark the start of a seizure episode (line 104), the start of an alarm condition (line 106), and the end of the major part of a seizure episode (line 108). As displayed from the base station user interface and FIG. 11, Z=4 and the alarm lag is 4 seconds for this example. Thus, an alarm condition may be initiated when Z≥4 for a period of greater than 4 seconds. In this Example the patient was monitored for a relatively short period of time during sleep. Monitoring the patient for greater periods of time or while the patient may engage in other activities, such as where other substantial signals may potentially be present, other detection settings, such as with greater values of the threshold Z and/or alarm lag may be used.

As illustrated in FIG. 13, the log periodogram of the seizure episode shows significantly higher amplitude as compared to a non-episode period. The x-axis in FIG. 13 is plotted with respect to the natural frequency and may be to a frequency in hertz. For example, as may be seen from FIG. 14, frequency ranges from about 300 Hz to about 400 Hz, from about 130 Hz to about 240 Hz, and from about 30 Hz to about 40 Hz may be particularly suitable for processing and analysis.

As shown in FIGS. 15-21, respectively, the EMG waveform filtered to pass seven different frequency ranges: 300-400 Hz, 130-240 Hz, 30-40 Hz, 10-50 Hz, 4-5 Hz, 3-4 Hz and 2-3 Hz is shown. As may be seen in FIGS. 15-18, the lower frequency ranges of 10-50 Hz, 4-5 Hz, 3-4 Hz and 2-3 Hz may show much more non-seizure muscle activity than the higher frequency bands for the reasons discussed above, namely, that lower frequency signals may be used to recruit muscles for activity, and that activity may or may not increase. Thus, those lower frequency ranges may be less suitable for use in detecting seizures and may result in an increased number of false alarms if used or given too much weight. Again, for illustration, three vertical lines are provided to mark the start of a seizure episode, the start of an alarm condition, and the end of the major part of a seizure episode. As may be seen from those waveforms, there may be occasional muscle activity having a high Z value, but that activity may not be sustained for a sufficient time to trigger an alarm condition.

Figure 17:
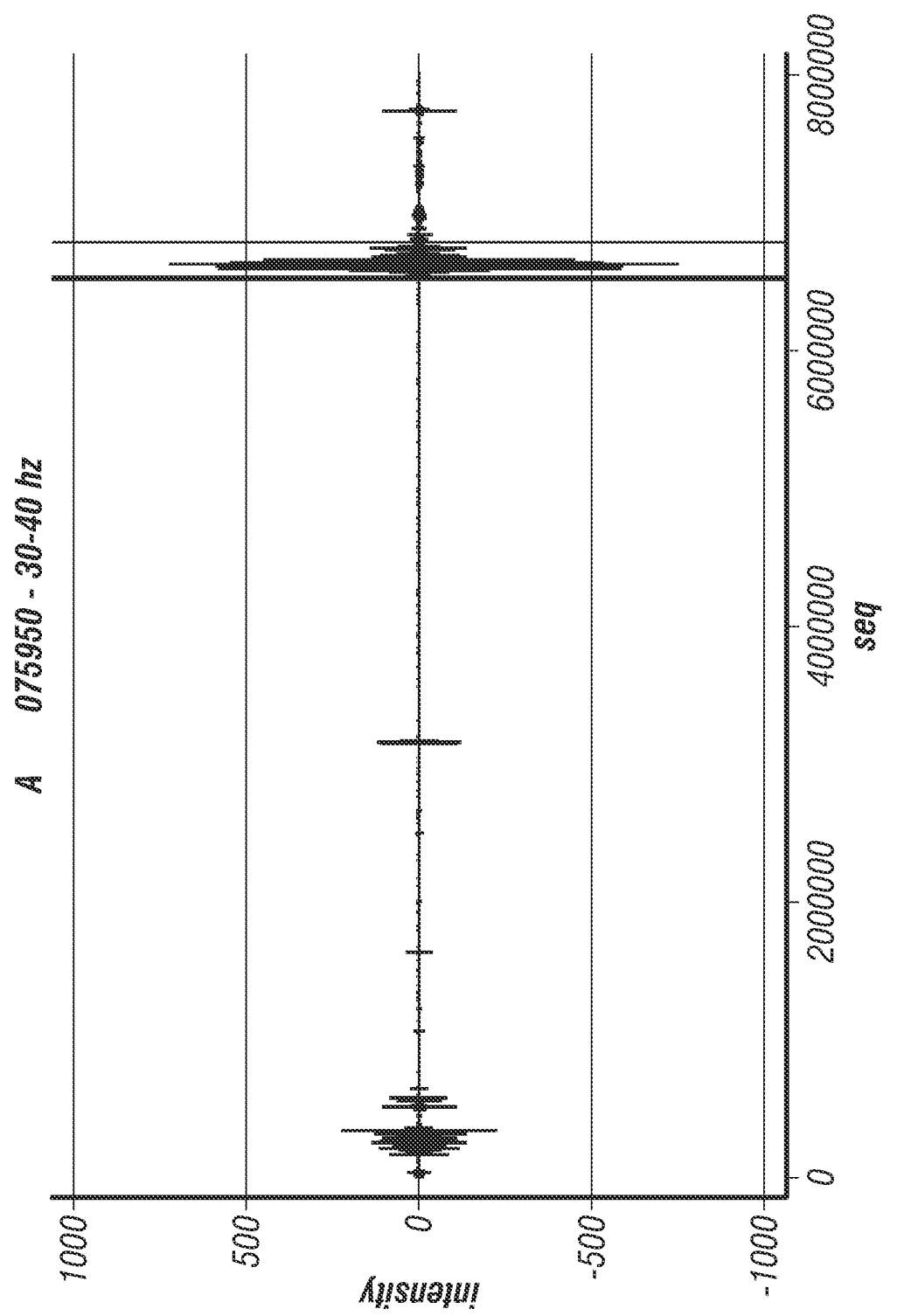
FIG. 17 illustrates the EMG waveform of FIG. 12 filtered to pass a frequency range of about 30-40 Hz.
Figure 18:
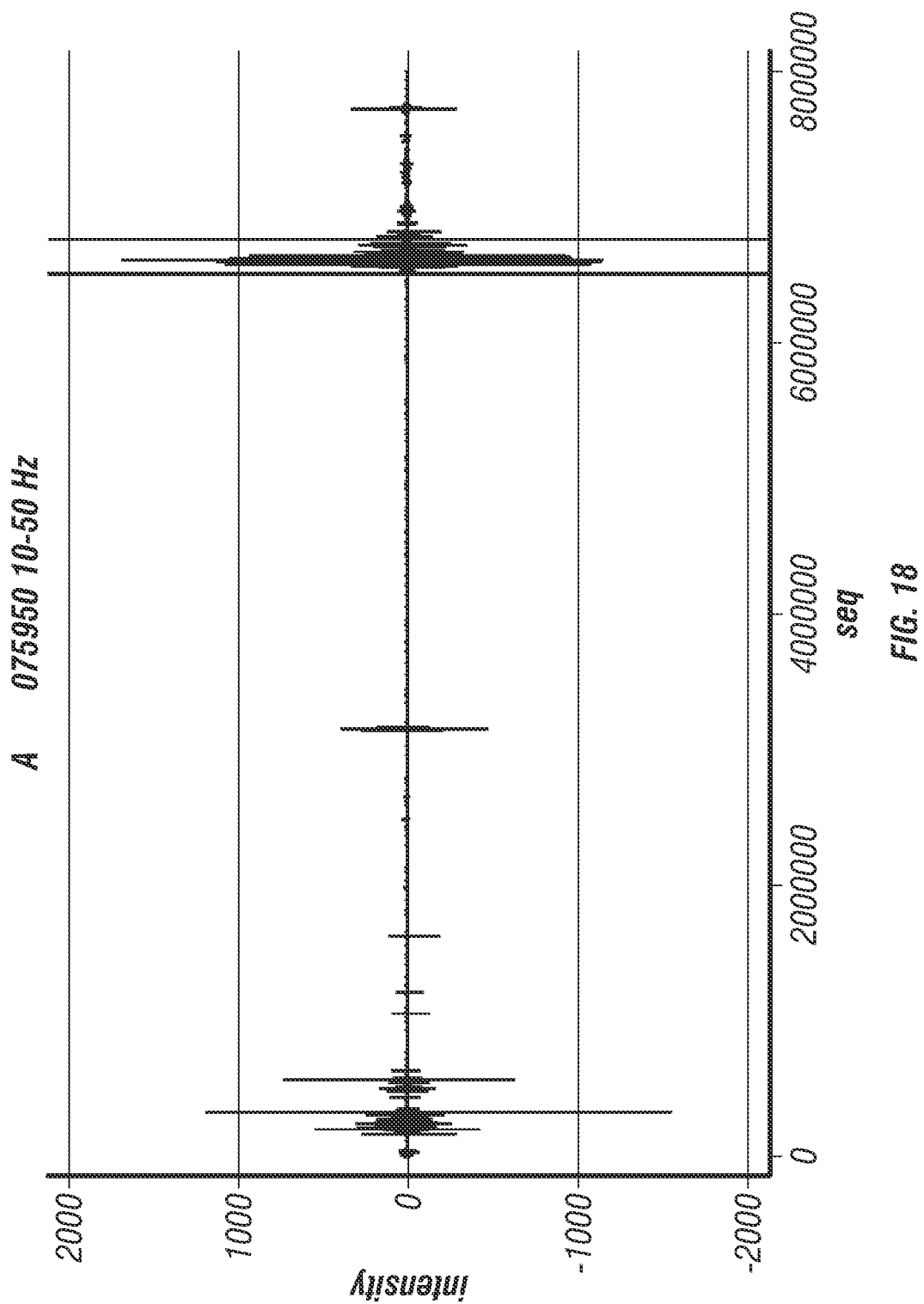
FIG. 18 illustrates the EMG waveform of FIG. 12 filtered to pass a frequency range of about 10-50 Hz.
Figure 19:
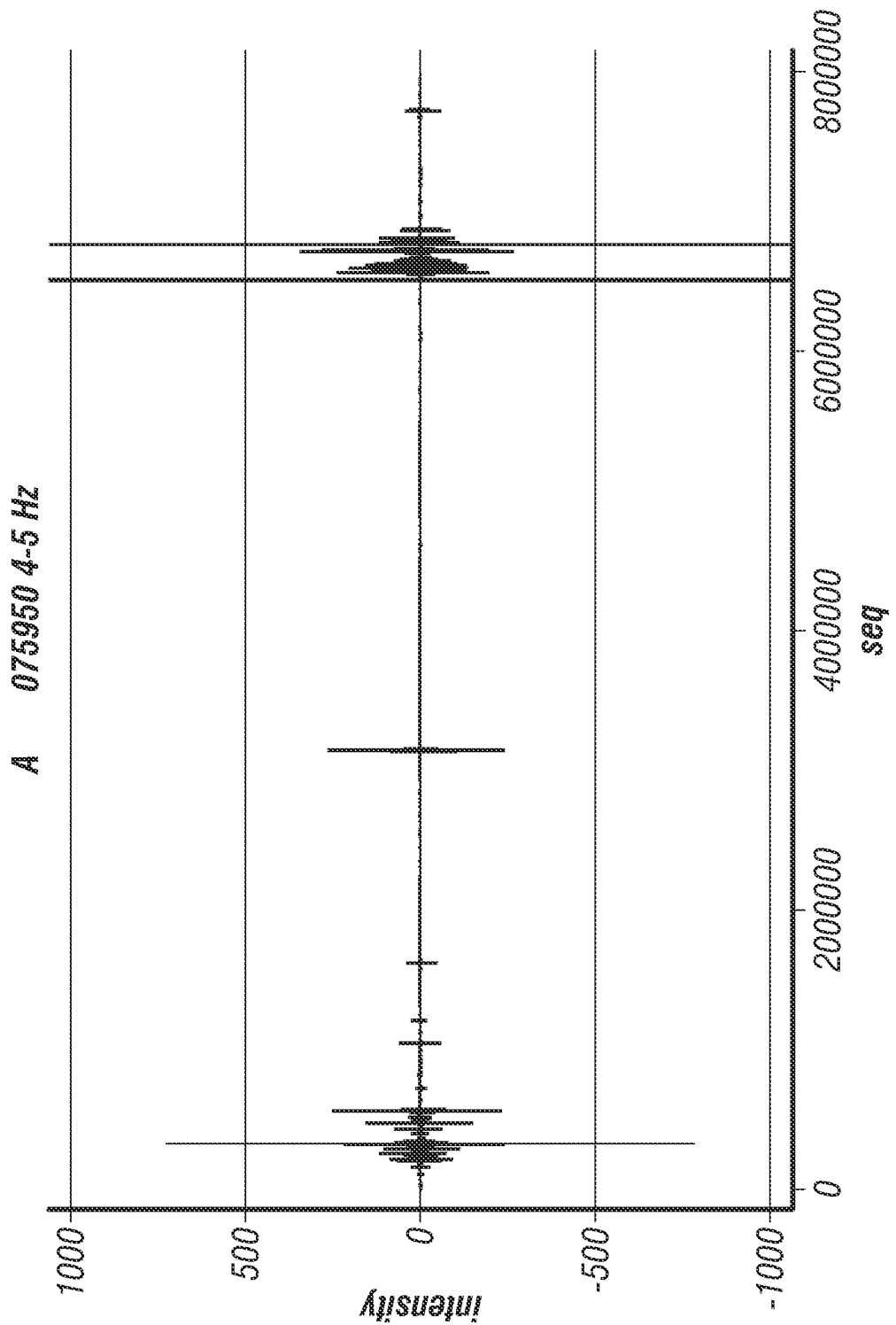
FIG. 19 illustrates the EMG waveform of FIG. 12 filtered to pass a frequency range of about 4-5 Hz.
Figure 20:
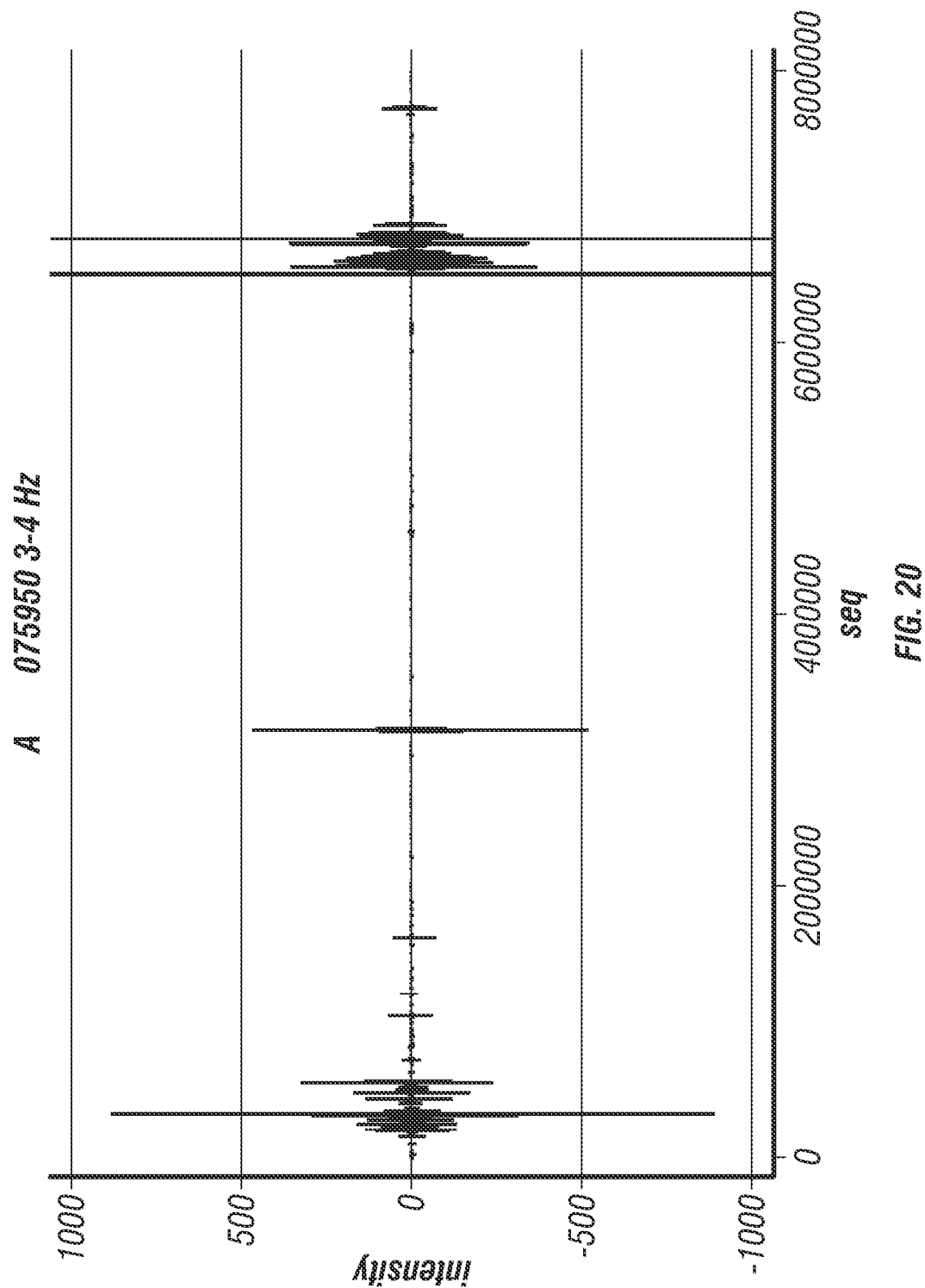
FIG. 20 illustrates the EMG waveform of FIG. 12 filtered to pass a frequency range of about 3-4 Hz.
Figure 21:
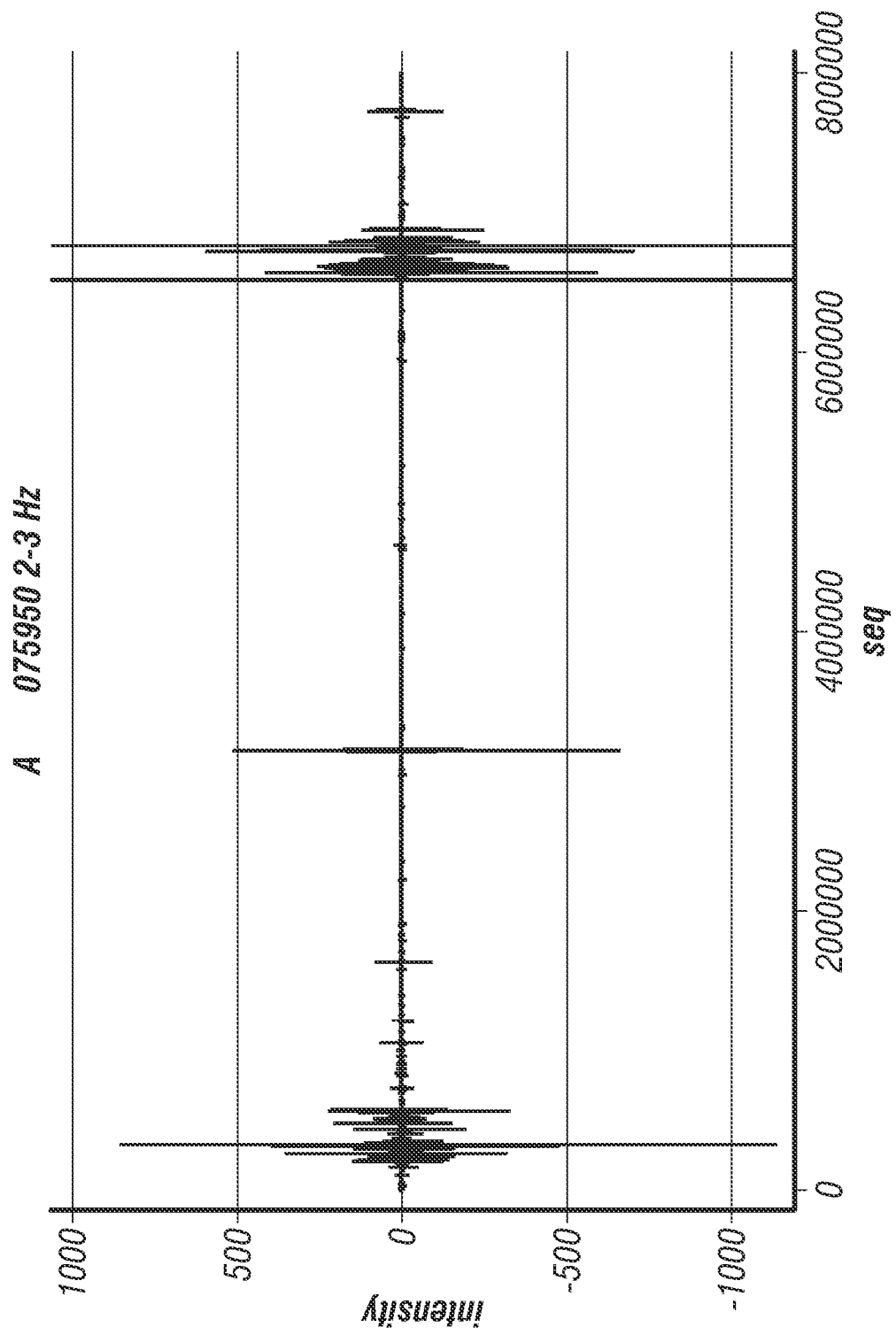
FIG. 21 illustrates the EMG waveform of FIG. 12 filtered to pass a frequency range of about 2-3 Hz.
Figure 22:
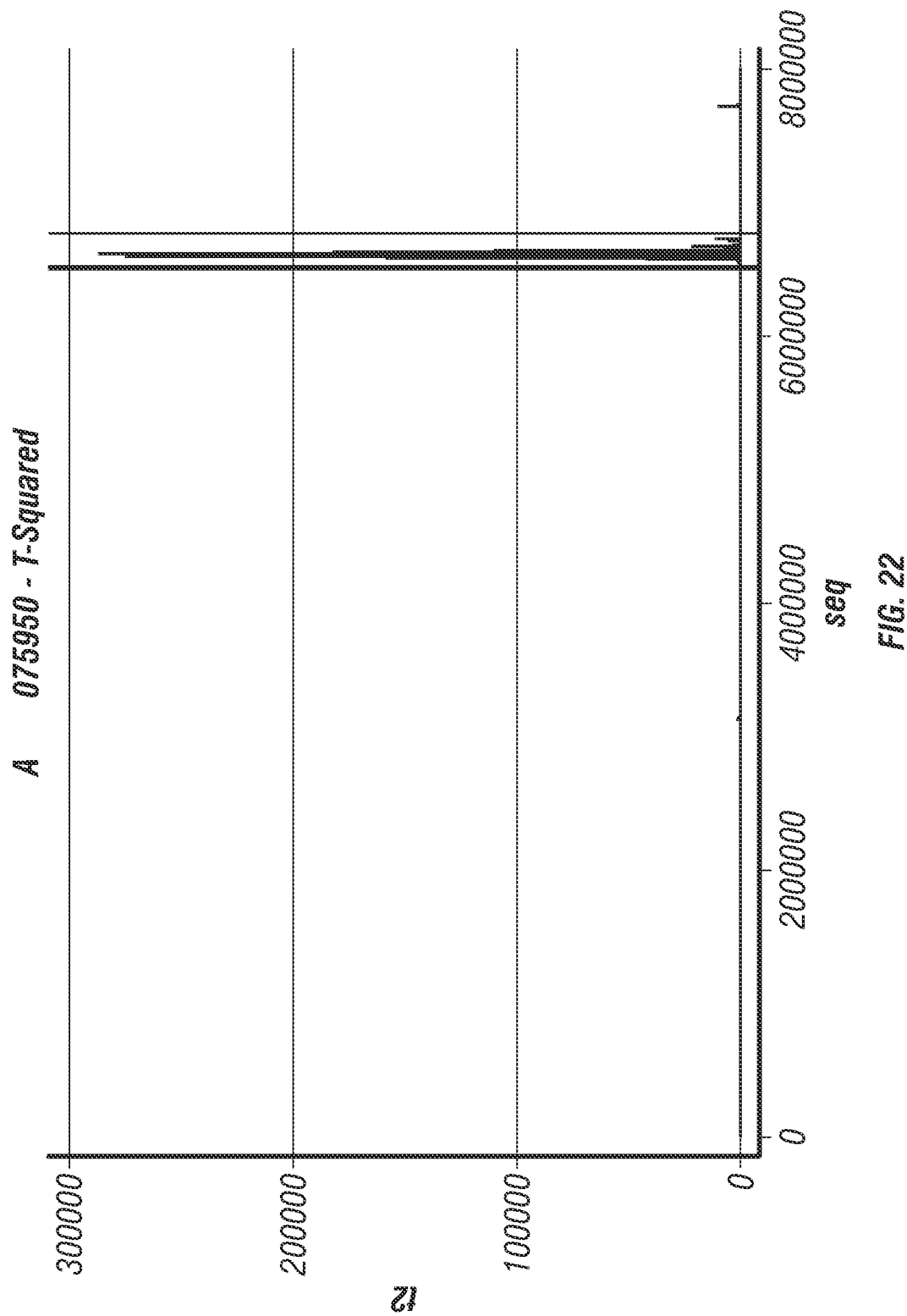
FIG. 22 illustrates the EMG the waveform of FIG. 12 after T-squared statistics has been calculated across various frequency ranges.
Figure 23:
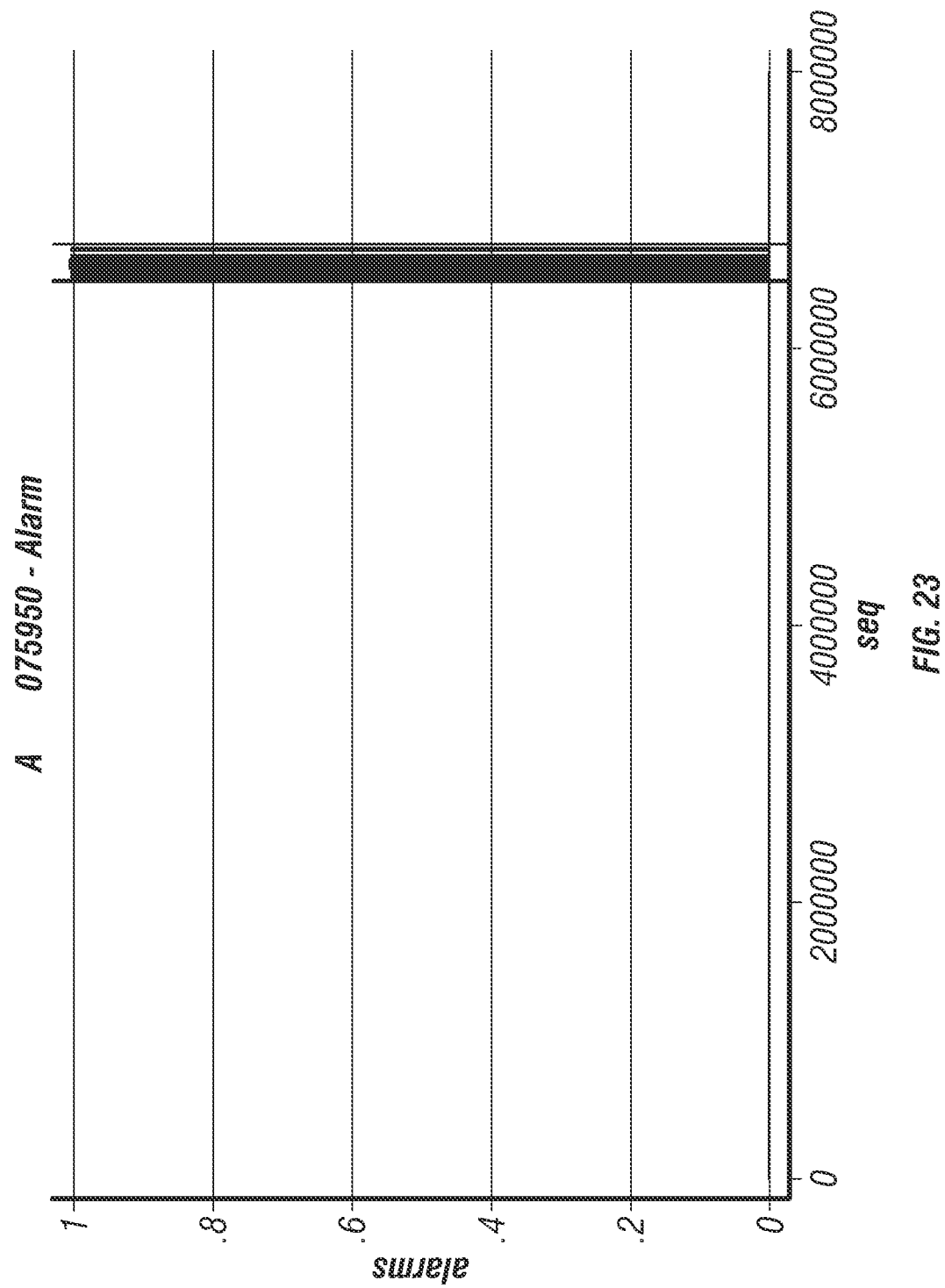
FIG. 23 illustrates the alarm state for the EMG waveform of FIG. 12.

FIG. 22 illustrates the waveform after T-squared statistics has been calculated across the three frequency ranges of 300-400 Hz (as may be seen in FIG. 15), 130-240 Hz (as may be seen in FIG. 16) and 30-40 Hz (as may be seen in FIG. 17). Again, for illustration, vertical lines are provided to mark the start and end of the seizure episode. When the T-squared calculation shows a Z value above the threshold of Z=4, the system may signal an alarm condition, as may be seen in the embodiment of FIG. 22, and sent an alert to a caregiver. As may be seen in the embodiment of FIG. 23, a chart of the T-squared alarm statistic indicates that the alarm state may be binary, i.e., may be zero except where an episode is recognized in which case the alarm state may be one.

EXAMPLE 2

In this Example 2, a total of 12 patients were each monitored for a period of about 4.4 days. Monitoring included using surface EMG electrodes and processing of data using the T-squared algorithm as described herein. The patients included 5 females and 7 male subjects, all of whom were mobile individuals. Of course, patients who are physically unable to walk may also be monitored. That is, in general, the discrimination between non-seizure motor manifestations and seizure activity for patients who are capable of movement and engaged in daily activities may be most challenging. In this study, the monitoring period included an overnight stay in a supervised setting. In addition to a portion of time where the patients were typically sleeping the monitoring period included a period of time where the patients were free to execute any of various common daily activities. For example, the patients were free to move (walk around), brush their teeth, comb their hair, watch TV or engage in any other desired activity. Those activities were verified to have been performed by the patients with video monitoring, which was also used as a check to verify the presence of any seizure activity. That is, in addition to monitoring with surface EMG electrodes, the patients were also monitored with inpatient scalp video-EEG (VEEG) recording.

For the EMG recordings, one arm of each patient was fitted to provide surface EMG recordings from muscles of the unilateral biceps and triceps brachii. However, while data from two muscle regions was collected, it has been found that data from either muscle group may be used individually. The EMG electrodes were bipolar Ag/AgCl electrodes and data was collected and streamed wirelessly for evaluation. For all of the patients in this study, three frequency bands were selected. Those frequency bands include a first band ranging from about 30-40 Hz, a second band ranging from about 130-240 Hz, and a third band ranging from about 300-400 Hz. EMG data was collected at the sampling rate of about 1,024 data points per second. Other detection settings were selected by characterization of electrode signals during a reference period. For example, a threshold T-squared value may be established to be about 100 standard deviations above a T-squared reference value derived from a training period. Such a value may be set by inputting a value of 100 for the threshold Z-factor. For the patients in this study threshold Z-factors were set to values between about 100 to about 1000. Alarm lag settings for the patients in this study were set to be between about 3 to about 10 seconds.

During monitoring, 6 of the 12 patients had a total of 7 GTC seizures. The monitoring system successfully detected all of the GTC seizures that were present. All of the seizures were detected within no more than about 10 seconds of any initial arm movement during a given GTC seizure (and generally within about 2 or about 3 seconds) of this movement. The system therefore provides almost immediate detection of a GTC seizure. Of course, the immediate detection of a GTC seizure may be important. Such may be particularly pertinent, for example, wherein detection of a seizure may be linked to stimulating devices that may be used to abort or attenuate a seizure. In addition, such may enable first responders (such as a parent or other caregiver) to be present as soon as possible during a seizure event. In addition, and despite the subjects being free to move about and conduct common daily activities, the system was able to detect seizures without initiation of a single false positive alarm.

EXAMPLE 3

In this Example 3, each of three patients was evaluated for seizure activity. Each of the patients was mobile and during the monitoring period of about 30 hours each was free to engage in common daily activities. Prior to the monitoring period, the patients were instructed to execute at least two maximum voluntary contractions. It should be noted that a fit patient may execute a plurality of maximum voluntary contractions, resting between executions, with little decline in muscle activity. For other patients, a smaller number of MVC executions may be performed before the patient becomes tired. Thus, the number of MVC executions that are conveniently executed in one reference period may be patient specific. While executing a MVC, EMG activity was collected and a T-squared value determined. For a first patient, mean T-squared values while executing two separate MVCs were about 742 and 809. For the first patient, one seizure was measured during the monitoring period. That seizure was found to provide a T-squared value of 2663—or about 3.4 times the average value of T-squared measured during the execution of the two MVCs. For a second patient, a T-squared value while executing an MVC was about 270. For the second patient, one seizure was measured during the monitoring period. That seizure was found to provide a T-squared value of 2386—or about 8.8 times the average value of T-squared measured during the execution of the two MVCs. For a third patient, mean T-squared values while executing two separate MVCs were about 570 and 668. For the third patient three seizures were measured during the monitoring period. Those seizures were found to provide T-squared value of 330302, 35767, and 53944. For patients who are active, a threshold T-squared value of about 100% of the MVC does not result in a significant number of false positives. For patients who are resting or patients who are physically impaired and not active a threshold T-squared value of about 50% of the MVC does not result in a significant number of false positives.

EXAMPLE 4

In this Example 4, a patient may be set up to be monitored in a home setting and a detection unit may be placed on the biceps and triceps. The monitoring system may include a remote transceiver element and additional transceivers associated with different locations in the patient's living space. A first environmental transceiver may be located on the patient's bed and a second environmental transceiver may be located in the patient's bathroom. When the patient is sleeping, a detector unit and first environmental transceiver may be operatively communicating. The system base station may receive a signal indicating this relationship and select a template file that is customized for that patient. The selected template file may be based on data collected for that patient while that patient is sleeping. The template file may include a Z lag setting that allows the patient to move while sleeping without initiating an alarm.

The patient may wake during sleep and walk to the bathroom. This movement may typically result in an elevated level of muscle movement. In addition, as the patient moves away from his or her bed, the positional relationship between the first environmental transceiver and the detection unit may be altered. The base station may receive an indication of that change in the position-dependent relationship and in response select a second template file for use. In this example 4, the second template file has a Z lag setting and weighting factors (such as a diminished weight associated with low and mid-level muscle activity) as appropriate to diminish the sensitivity of the system to an alarm. After going to the bathroom the patient may return to his or her bed and the positional relationship between the detection unit and the first environmental transceiver may be restored. The base station may receive an indication of the new position of the patient, e.g., the first environmental transceiver may send a pulse of information to the base station once it detects the presence of the detection unit, and select an appropriate template file, e.g., one associated with a patient sleeping in bed.

In some embodiments, a transceiver may additionally be mounted within a unit of furniture or some other structure, e.g., an environmental unit or object. If a detection unit is sufficiently close to that transceiver, such a transceiver may be capable of sending data to a base station. Thus, the base station may be aware that information is being received from that transducer, and therefore the associated environmental unit. In some embodiments, a base station may select a specific template file, e.g., such as including weighting factors between frequency regions or Z-factors used to evaluate whether an alarm is triggered or alarm lag settings or other data as described further herein, that is dependent upon whether or not it is receiving a signal from a certain transceiver. Thus, for example, if the base station receives information from a detector and from a transducer that is associated with a bed or crib, it may treat the data differently than if the data is received from a transducer associated with another.

Although the disclosed method and apparatus and their advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition, or matter, means, methods and steps described in the specification. Use of the word "include," for example, should be interpreted as the word "comprising" would be, i.e., as open-ended. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

We claim:

1. A system for monitoring a patient for seizure activity comprising:
    a detection unit mountable to said patient, the detection unit comprising:
        one or more electromyography electrodes configured to provide an electromyography signal representing seizure-related muscle activity;
        a first processor in communication with said one or more electromyography electrodes, said first processor configured to receive said electromyography signal, determine electromyography data from said electromyography signal, and process said electromyography signal to determine whether said seizure activity is occurring; and
        a transceiver in communication with said first processor, said transceiver configured to receive said electromyography data and to transmit said electromyography data if the first processor determines that said seizure activity is present;
    a base station configured to receive said electromyography data from said transceiver;
    one or more environmental transceivers associated with one or more objects present within a home setting for said patient, each of said one or more environmental transceivers being configured to transmit a proximity signal to said base station, the proximity signal being dependent upon whether a respective environmental transceiver among said one or more environmental transceivers is within an operating distance from said detection unit; and
    said base station comprising a second processor configured for:
        processing said proximity signal dependent upon whether the respective environmental transceiver among said one or more environmental transceivers is within an operating distance from said detection unit;
        based on said proximity signal, selecting a first template file among a plurality of template files, each of said plurality of template files including one or more seizure detection threshold settings;
        processing said electromyography data based on said one or more seizure detection threshold settings included in said first template file applied to confirm the presence of said seizure activity; and
        initiating transmission of an alarm to a remote caregiver if said seizure activity is confirmed.

2. The system of claim 1 further comprising:
    an input/output device included in said detection unit, said input/output device configured to allow said patient or an authorized party to activate said input/output device and to identify one or more occurrences when said detection unit determined that said seizure activity is present but that said patient or said authorized party determined that no seizure was actually occurring
wherein the second processor is further configured for:
automatically adjusting said one or more seizure detection threshold settings included in said first template file based on an identification of one or more times said patient or said authorized party activated said input/output device in order to establish one or more adjusted seizure detection threshold settings;
applying said one or more adjusted seizure detection threshold settings in a processing of recorded data from previous seizures that were correctly identified during a number of previous monitoring periods; and
calculating whether the applying of said one or more adjusted seizure detection threshold settings would have resulted in said system missing detection of any of said previous seizures.

3. The system of claim 2 wherein said second processor is further configured to apply the one or more adjusted seizure detection threshold settings to monitor said patient if said one or more adjusted seizure detection threshold settings would have correctly identified said previous seizures.

4. The system of claim 1 further comprising:
an input/output device included in said base station, said input/output device configured to allow said patient or said authorized party to activate said input/output device and identify occurrences when seizure activity was confirmed by said system but said patient or said authorized party determined that no seizure was actually occurring;
wherein the second processor is further configured for:
automatically adjusting said one or more seizure detection threshold settings included in said first template file based on an identification of one or more times said patient or said authorized party activated said input/output device in order to establish one or more adjusted seizure detection settings;
applying said one or more adjusted seizure detection settings in processing of recorded data from previous seizures that were correctly identified during a number of previous monitoring periods; and
calculating whether the applying of said one or more adjusted seizure detection settings would have resulted in the system missing detection of any of said previous seizures.

5. The system of claim 4 wherein said second processor is further configured to apply the one or more adjusted seizure detection settings to monitor said patient if said one or more adjusted seizure detection settings would have correctly identified said previous seizures.

6. The system of claim 5 wherein said one or more adjusted seizure detection settings are communicated to said first processor.

7. The system of claim 1 wherein said one or more objects include at least one of a crib, bed, chair, toilet, door, wall, toothbrush and an item of clothing.

8. The system of claim 1 wherein said one or more objects include an article of clothing customarily worn during physical exercise.

9. The system of claim 1 wherein said detection unit further comprises a microphone configured to record audio data, the detection unit being configured to transmit said audio data to said base station.

10. The system of claim 1 wherein said base station is further configured to send said electromyography data to a storage database.

11. A system for monitoring a patient for seizure activity comprising:
a detection unit mountable to a patient, the detection unit comprising:
one or more electromyography electrodes configured to provide an electromyography signal representing seizure-related muscle activity;
a first processor in communication with said one or more electromyography electrodes, said first processor configured to receive said electromyography signal, determine electromyography data from said electromyography signal, and process said electromyography signal to determine whether said seizure activity is present; and
a transceiver in communication with said first processor, said transceiver configured to receive said electromyography data and to transmit said electromyography data;
an input/output device in communication with a base station, said input/output device configured to allow said patient or said authorized party to activate said input/output device to identify occurrences when said seizure activity was either determined and/or confirmed by either of said detection unit and/or said base station but said patient or said authorized party determined that no seizure was actually occurring in order to identify false-positive detection events;
said base station configured to receive said electromyography data, the base station comprising a second processor configured for:
processing said electromyography data to confirm the presence of said seizure activity;
receiving a false-positive signal from said input/output device indicating any of said occurrences when no seizure was actually occurring; and
initiating sending of an alarm to a remote caregiver if said seizure activity is confirmed.

12. The system of claim 11 wherein the second processor is further configured for:
automatically adjusting one or more seizure detection threshold settings used to confirm the presence of said seizure activity based on an identification of one or more times said second processor received a false-positive signal from said input/ouput device in order to establish one or more adjusted seizure detection threshold settings.

13. The system of claim 12 wherein the second processor is further configured for:
applying said one or more adjusted seizure detection threshold settings in processing of recorded data from previous seizures that were correctly identified during a number of previous monitoring periods;
calculating whether said one or more adjusted seizure detection threshold settings would have resulted in the system missing detection of any of said previous seizures; and
verifying that use of said one or more adjusted seizure detection threshold settings would have resulted in detection of said previous seizures while minimizing false-positive detection events.

14. The system of claim 11 further comprising:
one or more environmental transceivers associated with one or more objects present within a home-setting for said patient, each of said one or more environmental transceivers being configured to transmit a proximity signal to said base station, the proximity signal being dependent upon whether the respective environmental transceiver is within a certain distance of said detection unit.

15. The system of claim 14 wherein said one or more objects include an article of clothing customarily worn during physical exercise.

16. The system of claim 14 wherein said one or more objects include at least one of a crib, bed, chair, toilet, door, wall, toothbrush and an item of clothing.

17. A method of monitoring a patient for seizure activity comprising:
  detecting an electromyography signal resulting from muscle motor activity of the patient using a mobile detection unit mounted to one or more of an arm band, adhesive tape, or item of clothing so as to allow positioning of one or more electromyography electrodes over a muscle of the patient;
  processing with a processor said electromyography signal to determine whether seizure activity is present;
  wherein the processing of said electromyography signal includes selection of one or more seizure detection thresholds included among a plurality of selectable seizure detection thresholds;
  identifying a location of the patient within a monitoring locale;
  wherein said selection of one or more seizure detection thresholds is based on said location of the patient.

18. The method of claim 17 further comprising:
  sending an environment signal to said processor;
  wherein said environment signal identifies said location of the patient;
  said environment signal being sent from one or more environmental transceivers associated with one or more objects present within a home-setting for said patient, said environment signal based on a position of said mobile detection unit with respect to at least one of said one or more environmental transceivers.

19. The method of claim 18 wherein said one or more environmental transceivers include a first environmental transceiver located in said patient's bathroom and a second environmental transceiver located on said patient's bed.

* * * * *